ized Patent

(12) United States Patent
Min et al.

(10) Patent No.: US 7,590,446 B1
(45) Date of Patent: Sep. 15, 2009

(54) METHODS FOR VENTRICULAR PACING

(75) Inventors: Xiaoyi Min, Thousand Oaks, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 22 days.

(21) Appl. No.: 10/986,273

(22) Filed: Nov. 10, 2004

Related U.S. Application Data

(63) Continuation of application No. 10/703,070, filed on Nov. 5, 2003, now abandoned.

(51) Int. Cl.
*A61N 1/362* (2006.01)
(52) U.S. Cl. .......................................................... 607/9
(58) Field of Classification Search ................ 607/9, 607/17, 25
See application file for complete search history.

(56) References Cited

U.S. PATENT DOCUMENTS

| | | | |
|---|---|---|---|
| 4,712,555 A | 12/1987 | Thornander et al. | 128/419 |
| 4,788,980 A | 12/1988 | Mann et al. | 128/419 |
| 4,928,688 A | 5/1990 | Mower | 128/419 PG |
| 4,940,052 A | 7/1990 | Mann et al. | 128/419 |
| 4,944,298 A | 7/1990 | Sholder | 128/419 |
| 5,086,774 A | 2/1992 | Duncan | 128/419 PG |
| 5,174,289 A | 12/1992 | Cohen | 128/419 PG |
| 5,179,949 A | 1/1993 | Chirife | |
| 5,391,189 A | 2/1995 | Van Krieken et al. | |
| 5,466,254 A | 11/1995 | Helland | 607/123 |
| 5,476,483 A | 12/1995 | Bornzin et al. | 607/17 |
| 5,643,327 A | 7/1997 | Dawson et al. | 607/24 |
| 5,741,308 A | 4/1998 | Sholder | 607/9 |
| 5,749,906 A | 5/1998 | Kieval et al. | |
| 5,800,465 A | 9/1998 | Thompson et al. | |
| 5,814,077 A | 9/1998 | Sholder et al. | 607/9 |
| 5,814,089 A | 9/1998 | Stokes et al. | |
| 5,873,895 A | 2/1999 | Sholder et al. | 607/9 |
| 6,122,546 A | 9/2000 | Sholder et al. | 607/9 |

(Continued)

FOREIGN PATENT DOCUMENTS

EP 1199085 A2 4/2002

(Continued)

OTHER PUBLICATIONS

Merino, J.L. MD et al., "Bundle-Branch Reentry and the Postpacing Interval After Entrainment by Right Ventricular Apex Stimulation," Circulation (2001), 103, pp. 1102-1108.

(Continued)

*Primary Examiner*—George R Evanisko
*Assistant Examiner*—Alyssa M Alter

(57) ABSTRACT

An exemplary method includes determining an atrial to ventricular activation time for a right ventricle; determining an atrial to ventricular activation time for a left ventricle; and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle, wherein, in the pacing sequence, pacing of the prior, paced ventricle occurs at a time based at least in part on a difference between the time for the right ventricle and the time for the left ventricle and an atrio-ventricular delay limit. Various other exemplary methods, devices and/or systems are also disclosed.

14 Claims, 18 Drawing Sheets

U.S. PATENT DOCUMENTS

| | | | |
|---|---|---|---|
| 6,141,588 A | 10/2000 | Cox et al. | |
| 6,144,880 A | 11/2000 | Ding et al. | 607/23 |
| 6,285,907 B1 | 9/2001 | Kramer et al. | 607/9 |
| 6,314,323 B1 | 11/2001 | Ekwall | |
| 6,360,127 B1 | 3/2002 | Ding et al. | 607/23 |
| 6,411,848 B2 | 6/2002 | Kramer et al. | 607/9 |
| 6,424,865 B1 | 7/2002 | Ding | 607/9 |
| 6,473,645 B1 | 10/2002 | Levine | |
| 6,473,647 B1 | 10/2002 | Bradley | |
| 6,496,730 B1 | 12/2002 | Kleckner et al. | |
| 6,567,700 B1 | 5/2003 | Turcott et al. | 607/9 |
| 6,606,516 B2 | 8/2003 | Levine | |
| 6,622,040 B2 | 9/2003 | Ding et al. | 607/9 |
| 6,668,194 B2 * | 12/2003 | VanHout | 607/9 |
| 6,754,530 B2 | 6/2004 | Bakels et al. | 607/14 |
| 6,804,555 B2 | 10/2004 | Warkentin | |
| 6,959,214 B2 | 10/2005 | Pape et al. | |
| 7,203,541 B2 | 4/2007 | Sowelam et al. | |
| 2001/0016759 A1 | 8/2001 | Kramer et al. | 607/9 |
| 2001/0031993 A1 | 10/2001 | Salo et al. | 607/9 |
| 2002/0049478 A1 | 4/2002 | Ding et al. | 607/17 |
| 2002/0062139 A1 | 5/2002 | Ding | 607/25 |
| 2002/0077559 A1* | 6/2002 | Ding et al. | 600/509 |
| 2002/0161410 A1 | 10/2002 | Kramer et al. | 607/9 |
| 2003/0004548 A1 | 1/2003 | Warkentin | |
| 2003/0014084 A1 | 1/2003 | VanHout | 607/9 |
| 2003/0060851 A1 | 3/2003 | Kramer et al. | 607/9 |
| 2003/0130702 A1 | 7/2003 | Kramer et al. | |
| 2003/0195580 A1 | 10/2003 | Bradley et al. | |
| 2003/0204212 A1 | 10/2003 | Burnes et al. | 607/17 |
| 2004/0133246 A1 | 7/2004 | Ding et al. | 607/9 |
| 2004/0147966 A1 | 7/2004 | Ding et al. | 607/9 |
| 2004/0193223 A1 | 9/2004 | Kramer et al. | 607/9 |
| 2005/0090870 A1 | 4/2005 | Hine et al. | |
| 2005/0149138 A1 | 7/2005 | Min et al. | |

FOREIGN PATENT DOCUMENTS

| | | |
|---|---|---|
| EP | 1234597 A2 | 8/2002 |
| EP | 0494487 B1 | 9/2007 |
| WO | WO 99/58191 | 11/1999 |
| WO | WO02/051495 | 7/2002 |
| WO | WO 03/037427 A1 | 8/2003 |
| WO | WO2005/039690 | 5/2005 |

OTHER PUBLICATIONS

Nelson, G.S. PhD et al., "*Left Ventricular or Biventricular Pacing Improves Cardiac Function at Diminished Energy Cost in Patients with Dilated Cardiomyopathy and Left Bundle-Branch Block*," Circulation (2000), 102, pp. 3053-3059.

Gerber, T.C. MD et al., "*Left Ventricular and Biventricular Pacing in Congestive Heart Failure*," Mayo Clinic Proc. (2001), 76, pp. 803-812.

Paul Wang et al., "*Timing Cycles for Biventricular Pacing*", PACE, 2002; vol. 25(1),pp.62-75.

Andreas Schuchert et al., "Effects of Body Position and Exercise on Evoked Response Signal for Automatic Threshold Activation," PACE, Oct. 1999; vol. 22, pp. 1476-1480.

Erich Ebner et al., "Ventricular Evoked Response as Clinical Marker for Hemodynamic Changes in Dilative Cardiomyopathy," PACE, Feb. 2004; vol. 27, pp. 166-174.

G. Schreier et al., "Correlation Between Changes in Stroke Volume and the Paced Intracardiac Electrogram," Jul. 2002; vol. 4, pp. 303-310.

R. Chirife et al., "Nonphysiological Left Heart AV Intervals as a Result of DDD and AAI "Physiological" Pacing ", PACE, Nov. 1991; vol. 14, Part II, pp. 1752-1756.

Raúl Chirife et al., "Automatic Beat-To-Beat Left Heart AV Normalization: Is it Possible?", PACE, Nov. 2003; vol. pp. 2103-2110.

Raul Chirife, "Proposal of a Method for Automatic Optimization of Left Heart Atrioventricular Interval Applicable to DDD Pacemakers", Jan. 1995; vol. 18, Part 1, pp. 49-56.

Raul Chirife, M.D., Letters to the Editor, PACE, May 2000; vol. 23, pp. 926.

Toshiyuki Ishikawa et al., "Prediction of Optimal Atrioventricular Delay in Patients with Implanted DDD Pacemakers", PACE, Sep. 1999; vol. 22, pp. 1365-1371.

NonFinal Office Action, mailed Nov. 17, 2005: Related U.S. Appl. No. 10/703,070.

Final Office Action, mailed Jul. 31, 2006: Related U.S. Appl. No. 10/703,070.

Advisory Action, mailed Oct. 20, 2006: Related U.S. Appl. No. 10/703,070.

NonFinal Office Action, mailed Apr. 10, 2007: Related U.S. Appl. No. 10/703,070.

NonFinal Office Action, mailed Apr. 10, 2007: Related U.S. Appl. No. 10/974,123.

NonFinal Office Action, mailed Oct. 9, 2007: Related U.S. Appl. No. 10/980,140.

Ismer, B. et al, "Impact of Discriminating Electrophysiological and Electromechanical Determinants of the Optimal AV Delay in Right and Biventricular DDD Pacing," Folia Cardiol. 2006, tom 13, supl. C.

* cited by examiner

EXEMPLARY AR RHYTHMS
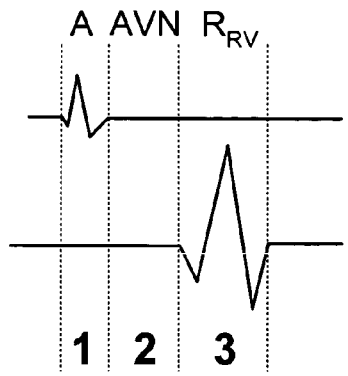
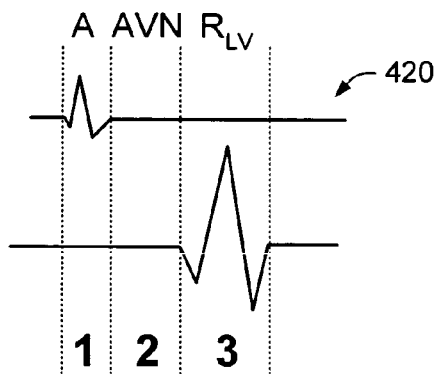
$AR_{RV} = R_{RV} - A$  $AR_{LV} = R_{LV} - A$
$\Delta = AR_{LV} - AR_{RV}$
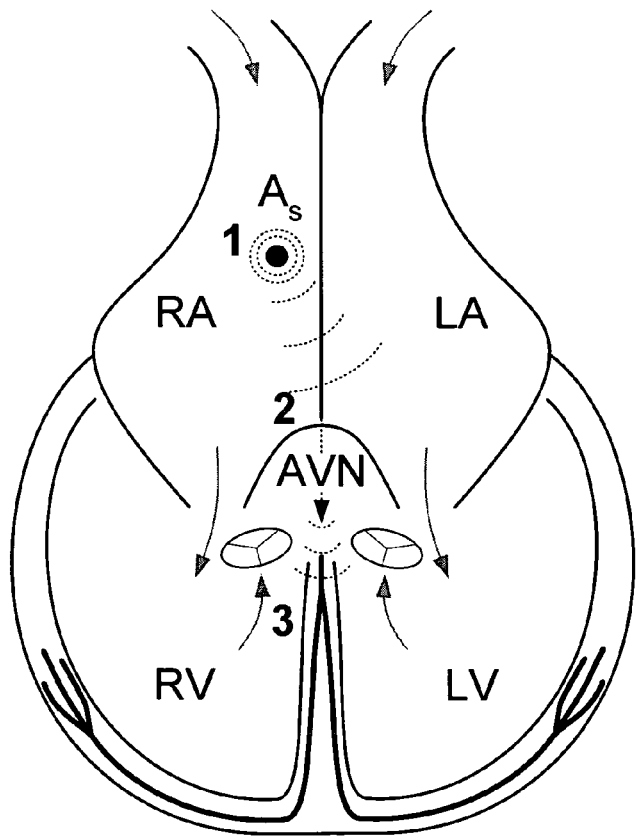
Fig.4

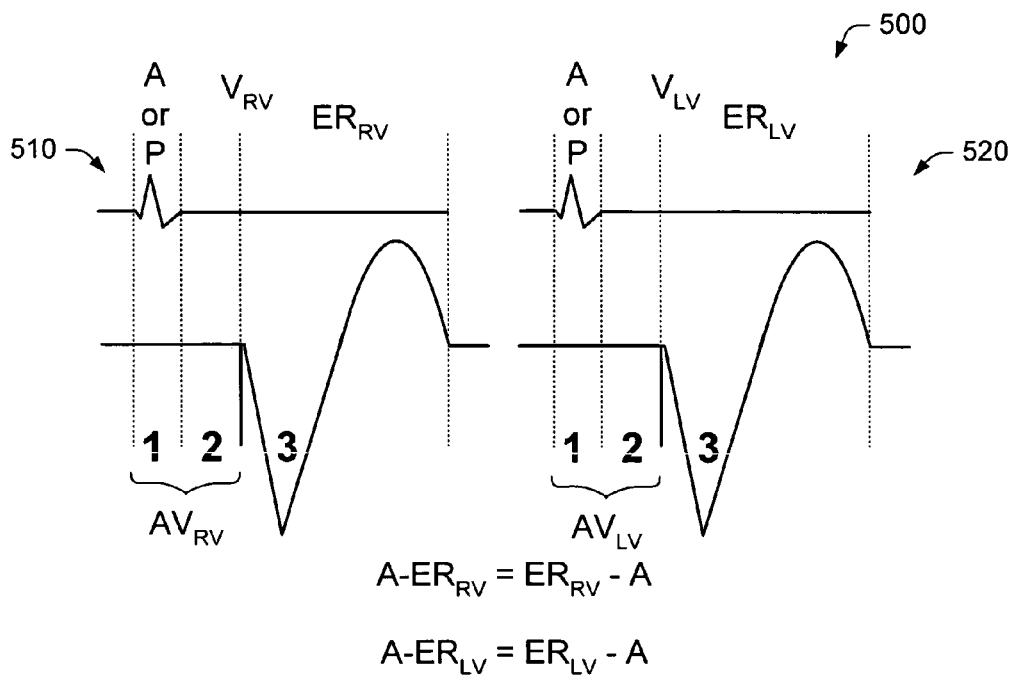
$A\text{-}ER_{RV} = ER_{RV} - A$
$A\text{-}ER_{LV} = ER_{LV} - A$
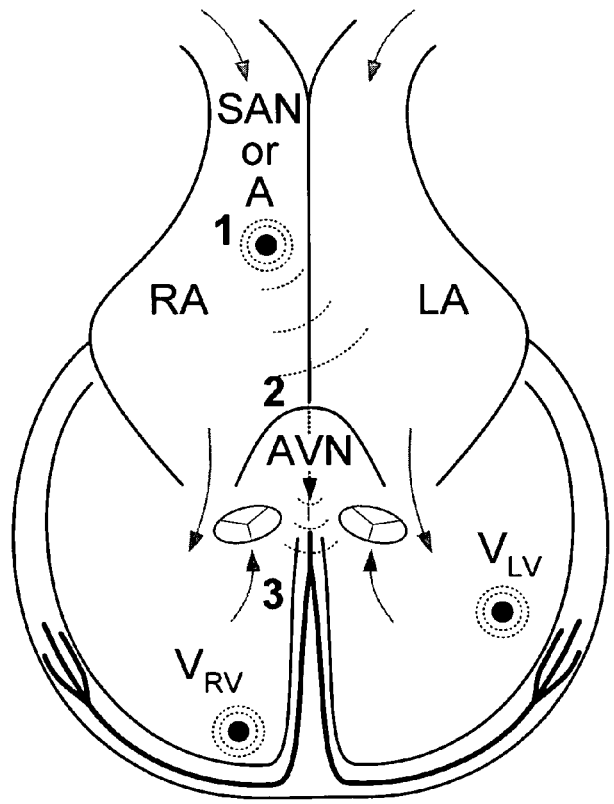
Fig.5

$\Delta = AR_{LV} - AR_{RV}$ or $PR_{LV} - PR_{RV}$ $\quad \Delta_{programmed} = AV_{LV} - AV_{RV}$ or $PV_{LV} - PV_{RV}$ $\Delta(610) = -40$ ms, $\Delta_{optimal}(610) = -20$ ms $\quad \Delta(620) = -80$ ms, $\Delta_{optimal}(620) = -40$ ms $$\alpha = \Delta_{optimal} / \Delta$$

$\alpha\ (610) = \Delta_{optimal} / \Delta = -20$ ms $/ -40$ ms $= 0.5$ $\alpha\ (620) = \Delta_{optimal} / \Delta = -40$ ms $/ -80$ ms $= 0.5$

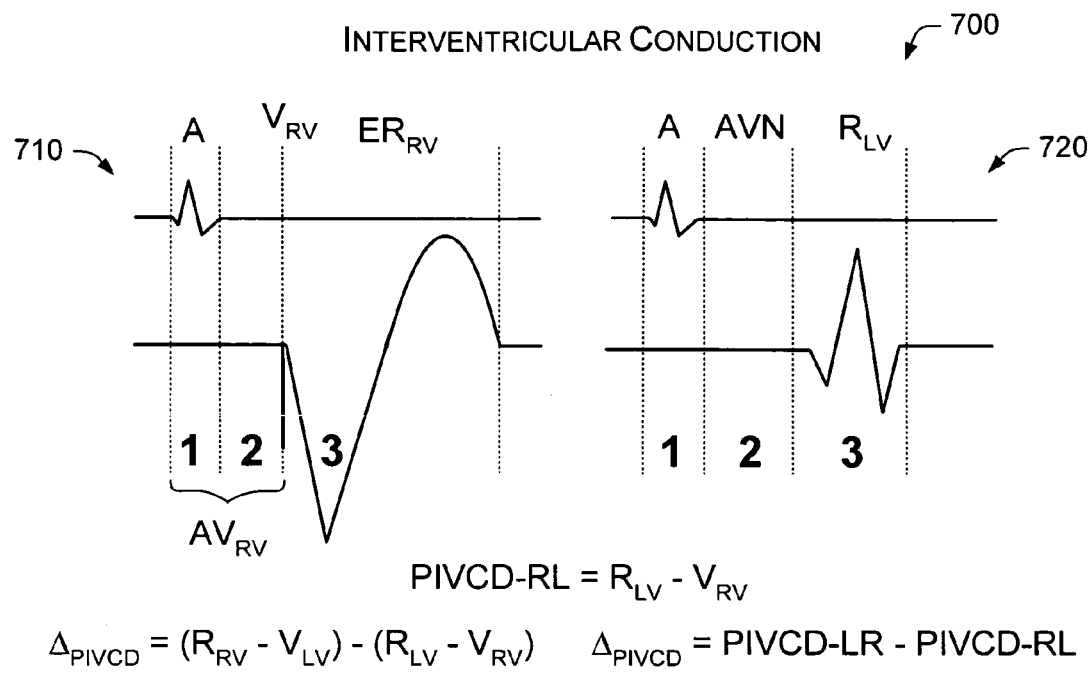
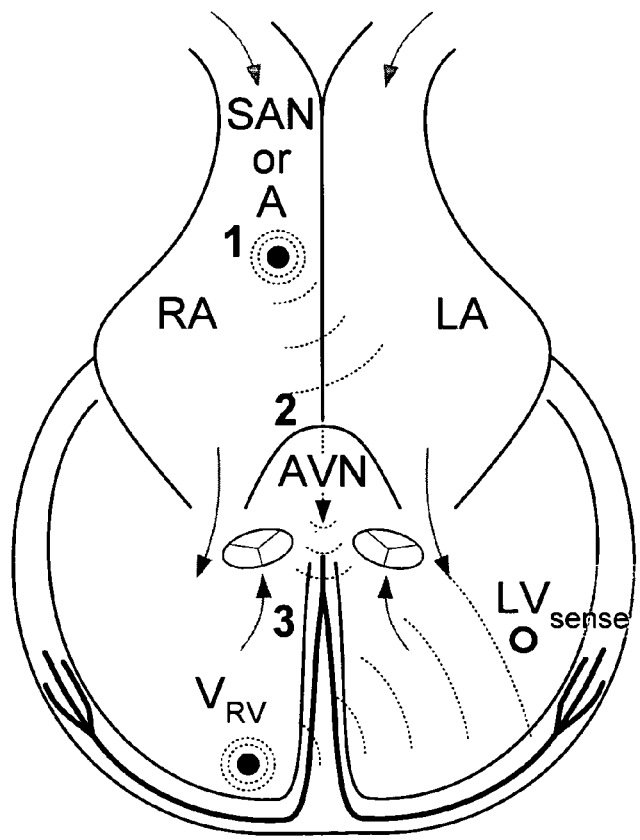
Fig.7

Exemplary Scenarios

Scenario I: $AR_{LV}$ or $AR_{RV} > AR_{max}$

Action: Pace in Ventricle with $AR > AR_{max}$

Scenario II: $AR_{LV}$ and $AR_{RV} > AR_{max}$

Action: Pace in both Ventricles

Scenario III: $AR_{LV}$ and $AR_{RV} < AR_{max}$

Action: No Pacing in Ventricles or Other Appropriate Actions

Fig. 9

EXEMPLARY SCENARIOS 1000

<u>Scenario I</u>:   $AR_{LV}$ or $AR_{RV} > AR_{max}$

Action:   Pace in Ventricle with $AR > AR_{max}$

If $AR_{LV} > AR_{max}$, then Left Bundle Branch Block and pace early in Left Ventricle.

$$\text{If } |\Delta_{PIVCD}| < \varepsilon,$$
$$\text{then } AV_{LV} = AV_{optimal} - |\Delta|$$

$$\text{If } |\Delta_{PIVCD}| \geq \varepsilon,$$
$$\text{then } AV_{LV} = AV_{optimal} - (|\Delta| + \Delta_{PIVCD})$$

If $AR_{RV} > AR_{max}$, then Right Bundle Branch Block and pace early in Right Ventricle.

$$\text{If } |\Delta_{PIVCD}| < \varepsilon,$$
$$\text{then } AV_{RV} = AV_{optimal} - |\Delta|$$

$$\text{If } |\Delta_{PIVCD}| \geq \varepsilon,$$
$$\text{then } AV_{RV} = AV_{optimal} - (|\Delta| - \Delta_{PIVCD})$$

Fig.10

EXEMPLARY SCENARIOS  1100

Scenario II: $AR_{LV}$ and $AR_{RV} > AR_{max}$

Action: Pace in both Ventricles

If $AR_{LV} > AR_{RV}$, then:
    (a) set $AV_{RV}$ to $AV_{Optimal}$ and
    (b) pace early in Left Ventricle.

If $|\Delta_{PIVCD}| < \varepsilon$,
        then $AV_{LV} = AV_{RV} - |\Delta|$ If $|\Delta_{PIVCD}| \geq \varepsilon$,
        then $AV_{LV} = AV_{RV} - (|\Delta| + \Delta_{PIVCD})$ If $AR_{RV} > AR_{LV}$, then:
    (a) set $AV_{LV}$ to $AV_{Optimal}$ and
    (b) pace early in Right Ventricle.

If $|\Delta_{PIVCD}| < \varepsilon$,
        then $AV_{RV} = AV_{LV} - |\Delta|$ If $|\Delta_{PIVCD}| \geq \varepsilon$,
        then $AV_{RV} = AV_{LV} - (|\Delta| - \Delta_{PIVCD})$

Fig.11

EXEMPLARY SCENARIOS  ⟵ 1200

Scenarios I or II $AR_{LV} > AR_{RV}$

If $|\Delta_{PIVCD}| < \varepsilon$,
        then $AV_{LV} = AV_{optimal} - \alpha|\Delta|$ If $|\Delta_{PIVCD}| \geq \varepsilon$,
        then $AV_{LV} = AV_{optimal} - \alpha(|\Delta| + \Delta_{PIVCD})$ $AR_{RV} > AR_{LV}$ If $|\Delta_{PIVCD}| < \varepsilon$,
        then $AV_{RV} = AV_{optimal} - \alpha|\Delta|$ If $|\Delta_{PIVCD}| \geq \varepsilon$,
        then $AV_{RV} = AV_{optimal} - \alpha(|\Delta| - \Delta_{PIVCD})$

Fig. 12

METHODS FOR VENTRICULAR PACING

CROSS-REFERENCE TO RELATED APPLICATIONS

This application is a continuation of copending U.S. patent application Ser. No. 10/703,070, titled "Methods for Ventricular Pacing," filed on Nov. 5, 2003.

TECHNICAL FIELD

Exemplary methods and/or devices presented herein generally relate to cardiac pacing and/or stimulation therapy. Various exemplary methods and/or devices concern ventricular sensing and adaptive ventricular pacing.

BACKGROUND

Clinical studies related to cardiac pacing have shown that an optimal atrio-ventricular delay (e.g., AV delay) and/or an optimal interventricular delay (e.g., VV delay) can improve cardiac performance. However, such optimal delays depend on a variety of factors that may vary over time. Thus, what is "optimal" may vary over time. An optimization of AV delay and/or VV delay may occur at implantation and sometimes, a re-optimization may occur during a follow-up consultation. While such optimizations are beneficial, the benefits may not be long lasting due to changes in various factors related to device and/or cardiac function. As described herein, various exemplary methods, devices and/or systems aim to determine and/or adjust AV delay, VV delay and/or other interchamber delays.

Inappropriate sensing is another issue germane to cardiac pacing. For example, the incidence of double counting from ventricular sensing may be significant in some situations and result in false detections and delivery of inappropriate therapies (e.g., tachycardia therapies, etc.). As described herein, various exemplary methods, devices and/or systems aim to reduce the risk of double counting or inappropriate cross-sensing of ventricular signals.

SUMMARY

An exemplary method includes determining an atrial to ventricular activation time for a right ventricle; determining an atrial to ventricular activation time for a left ventricle; and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle, wherein, in the pacing sequence, pacing of the prior, paced ventricle occurs at a time based at least in part on a difference between the time for the right ventricle and the time for the left ventricle and an atrio-ventricular delay limit. Various other exemplary methods, devices and/or systems are also disclosed.

Various exemplary devices and/or systems for performing such exemplary methods are also disclosed herein along with a variety of other exemplary methods, devices and/or systems. In general, the various methods, devices and/or systems described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

FIG. 4 is an approximate anatomical diagram of a heart and two IEGM waveforms that exhibit an A wave and an R wave.

FIG. 5 is an approximate anatomical diagram of a heart and two sets of IEGM waveforms that include an A or P wave on an atrial sensing channel and evoked response on a ventricular sensing channel.

FIG. 7 is an approximate anatomical diagram of a heart and two sets of IEGM waveforms wherein one set includes an evoked response in a right ventricle and the other set includes a response from a conducted event in a left ventricle.

FIG. 9 is of various exemplary scenarios labeled Scenario I, Scenario II and Scenario III, which are related to cardiac therapy and, in particular, ventricular pacing.

FIG. 10 is of various exemplary equations related to Scenario I of FIG. 9, which may be indicative of left bundle branch block or right bundle branch block.

FIG. 11 is of various exemplary equations related to Scenario II of FIG. 9, which may be indicative of left bundle branch block or right bundle branch block.

FIG. 12 is of various exemplary equations related to Scenario I and/or Scenario II of FIG. 9, wherein an exemplary parameter such as $\alpha$ of FIG. 6 may be used to one or more determine pacing delays.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary methods, devices and/or systems pertain generally to ventricular pacing. For example, various exemplary methods include deciding whether to use ventricular pacing and, if so, whether to pace in a single ventricle or in both ventricles. If such a method decides that ventricular pacing is appropriate, then the method may also determine an atrioventricular delay for one or both ventricles. For the case of bi-ventricular pacing, the method may determine an atrioventricular delay for each ventricle and/or an interventricular delay (e.g., which may be inherent in the use of two atrioventricular delay times). Such a method may reduce frequency of ventricular or bi-ventricular pacing and/or enhance cardiac performance. Further, such a method may optimize pacing as a function of time or in response to changes in any of a variety of factors related to cardiac and/or device performance.

With respect to cardiac performance, various exemplary methods, devices and/or systems include an adjustable cardiac performance parameter. Such a performance parameter is optionally determined via cardiac testing. As described below, echocardiogram testing or other hemodynamic sensors (e.g., pressure, etc.) may be used to determine an optimal interventricular pacing delay suitable for use in bi-ventricular pacing. In this example, the performance parameter may be a function of this delay and an intrinsic interventricular conduction delay, which may be measured in vivo. Various exemplary methods, devices and/or systems may make adjustments to pacing therapy based on information from in vivo electrocardiogram sensing. Such methods, devices and/or systems may or may not include other sensors such as hemodynamic sensors.

The following description begins with a discussion of exemplary implantable devices and associated components followed by a discussion of heart rhythms and associated waveforms. Next, a discussion of cardiac performance follows, and the detailed description continues with a discussion of various exemplary methods, devices and/or systems.

Exemplary Stimulation Device

The techniques described below are intended to be implemented in connection with any stimulation device that is configured or configurable to stimulate nerves and/or stimulate and/or shock a patient's heart.

Figure 1:
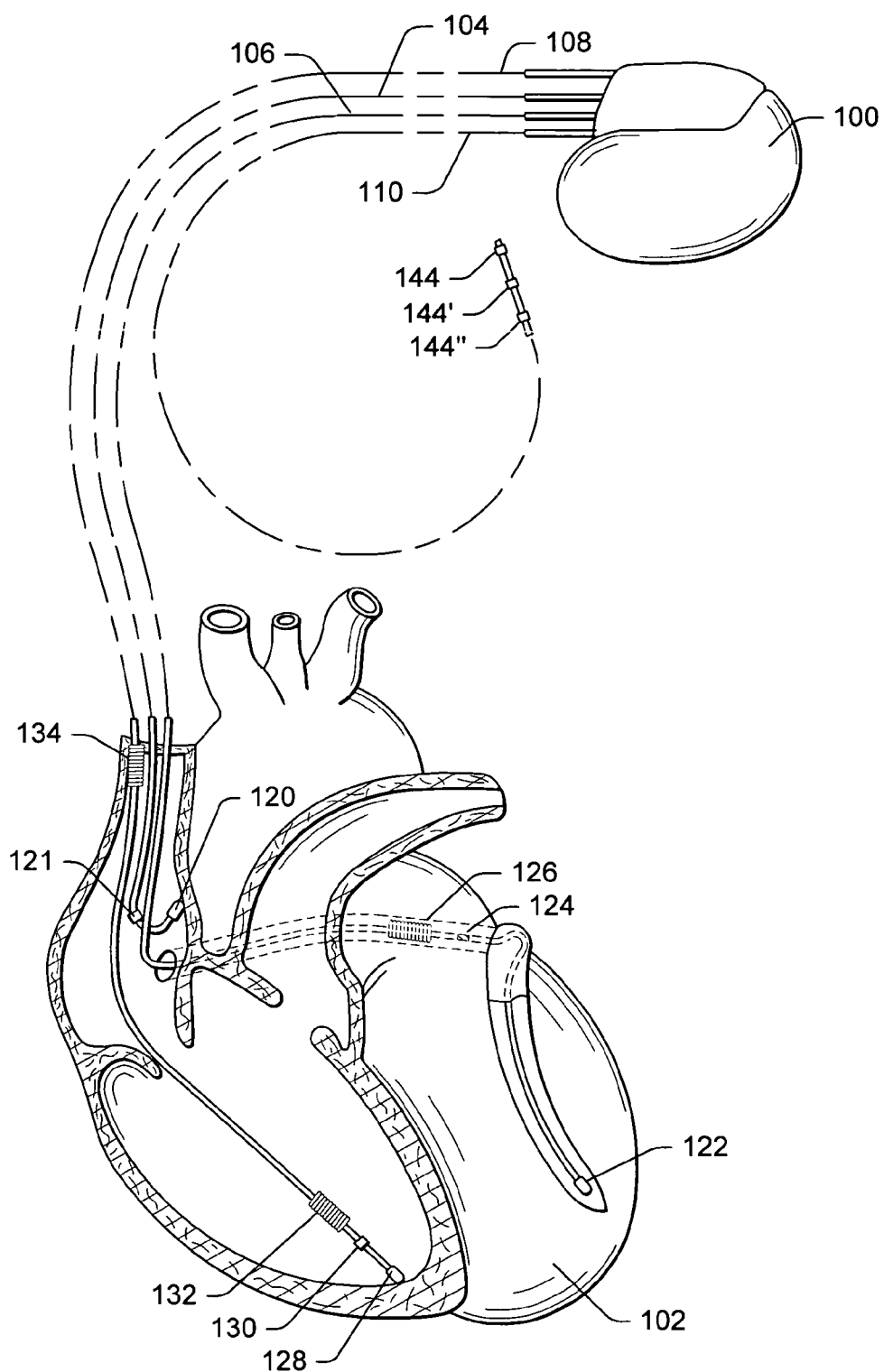
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve such an electrode may be positioned on the lead or a bifurcation or leg of the lead.

Figure 2:
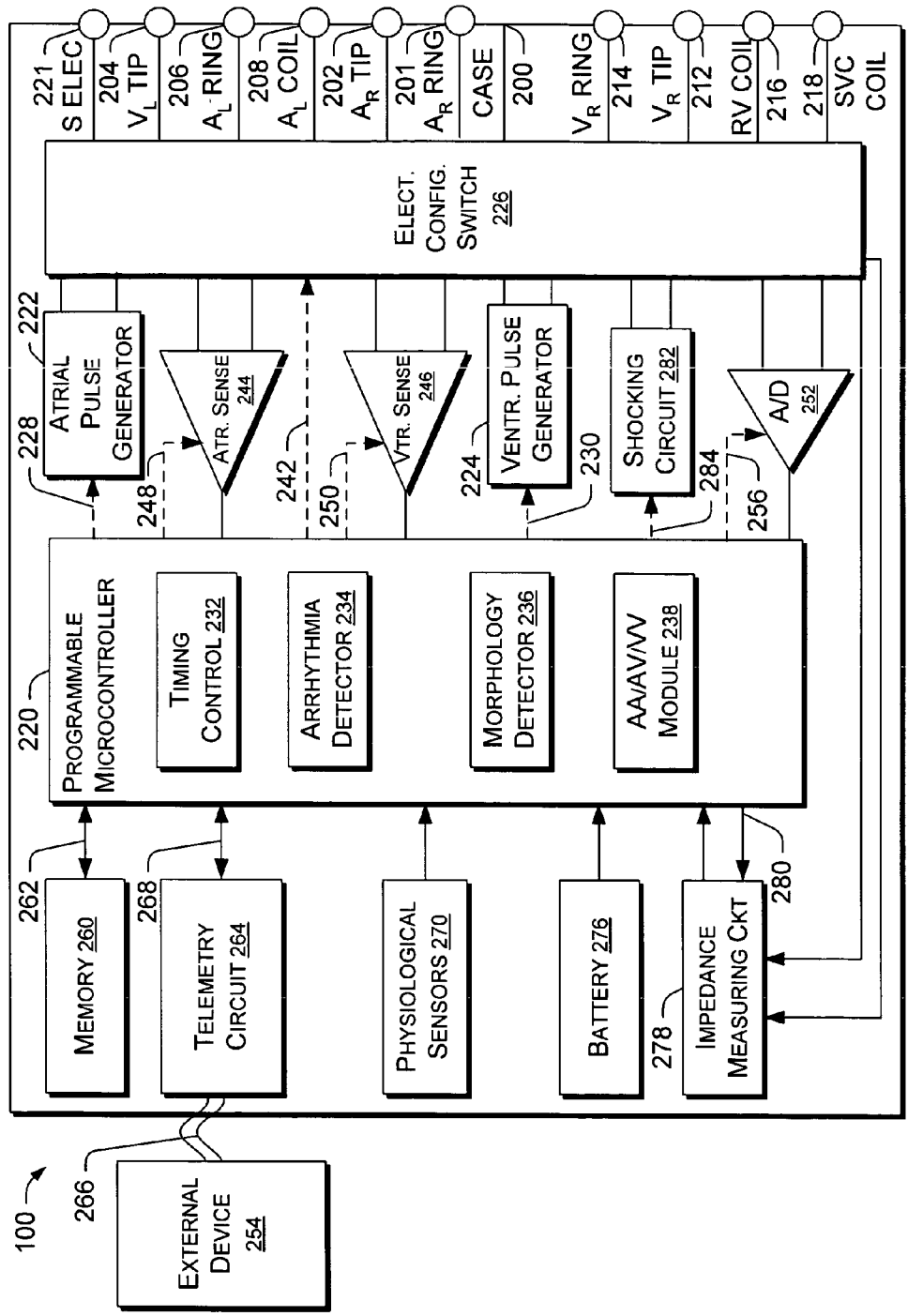
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module; the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, biventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythms

Figure 3:
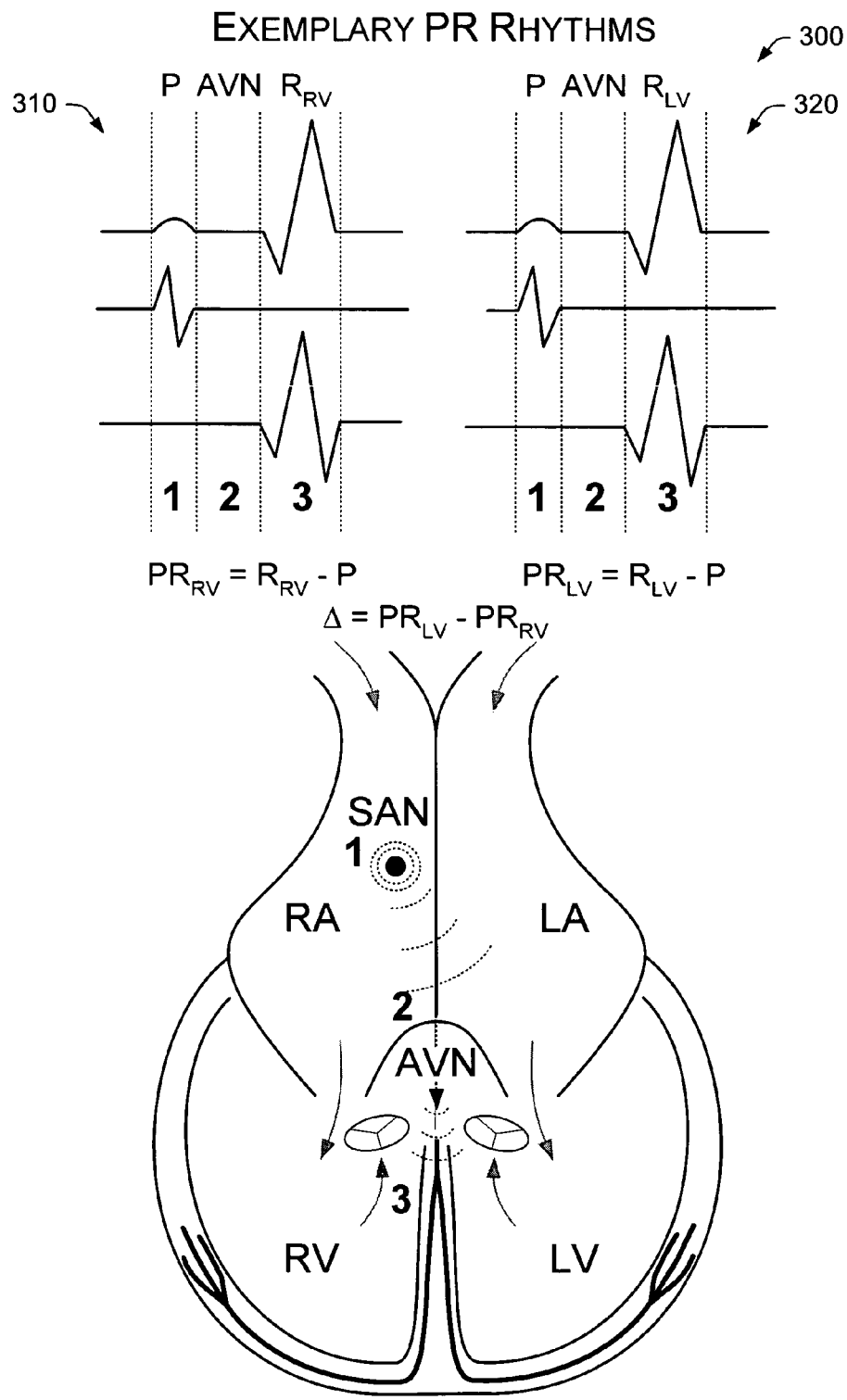
FIG. 3 is an approximate anatomical diagram of a heart, a surface ECG and two IEGM waveforms that exhibit an intrinsic P wave and an R wave.

FIG. 3 shows an approximate anatomical diagram of a heart and two sets of PR waveforms 300. One set of waveforms 310 corresponds in part to right ventricular activity while another set of waveforms 320 corresponds in part to left ventricular activity. Action potentials propagating through a normal heart are labeled as follows: 1, associated with the sinoatrial node (SAN) and the atria; 2, associated with the atrio-ventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

FIG. 3 also shows two surface electrocardiograms (ECG) of normal heart activity (e.g., polarization, depolarization, etc.) wherein atrial depolarization is represented as a "P wave" and ventricular depolarization is represented as an "R wave", or QRS complex. The right ECG shows a P wave followed by an AVN conduction delay (AVN) and a right ventricular R wave or QRS complex ($R_{RV}$). The left ECG shows a P wave followed by an AVN conduction delay (AVN) and a left ventricular R wave or QRS complex ($R_{LV}$). In this example, the right and left ventricular R waves ($R_{RV}$ and $R_{LV}$) are due to conduction through the atrio-ventricular node and not due to artificially paced events. The sets of plots 310, 320 include approximate atrial IEGM waveforms and approximate ventricular IEGM waveforms, for example, as sensed by an atrial sensing channel and one or more ventricular sensing channels.

Often detection of an R wave or QRS complex in an IEGM relies on signal amplitude or signal derivative with respect to time. Further, many detection methods are capable of assigning a time to a detected R wave or QRS complex or assigning a time span to a P wave to R wave or QRS complex interval, which are shown in FIG. 3 as $PR_{RV}$ for the right ventricle and $PR_{LV}$ for the left ventricle. If $PR_{RV}$ and $PR_{LV}$ are approximately equal, then the right ventricle and the left ventricle contract in a synchronous manner. For example, in a normal heart, the delay between contraction of the right ventricle and the left ventricle may be around 5 ms. However, if $PR_{RV}$ and $PR_{LV}$ differ substantially, e.g., $|\Delta|=|PR_{LV}-PR_{RV}|>5$ ms, then the right ventricle and left ventricle contract in an asynchronous manner, which may indicate some degree of cardiac dysfunction. Depending on patient or other factors, the time could be set at some time other than 5 ms.

The variable $\Delta$ represents an interventricular delay that is based on an atrio-ventricular delay for the left ventricle ($PR_{LV}$) and an atrio-ventricular delay for the right ventricle ($PR_{RV}$). The variable $|\Delta|$ is shown as the absolute value of the difference while herein and in the figures the variable $\Delta$ (e.g., $\Delta=PR_{LV}-PR_{RV}$) may be less than zero when $PR_{RV}$ exceeds $PR_{LV}$ or greater than zero when $PR_{LV}$ exceeds $PR_{RV}$. Described further below is a variable referred to as a paced interventricular conduction delay ($\Delta_{PIVCD}$), which relies on pacing in one ventricle and sensing in the other ventricle and optionally vice versa.

With respect to cardiac condition, a long interventricular delay may be indicative of a conduction block. For example, left bundle branch block (LBBB) may cause the left ventricle to contract more than approximately 50 ms after contraction of the right ventricle (e.g., $\Delta>0$). Whereas a right bundle branch block (RBBB) may be expected to cause the right ventricle to contract well after the left ventricle (e.g., $\Delta<0$). Of course, a patient may have RBBB and LBBB of similar extent such that interventricular delay does not indicate whether a block could be RBBB or LBBB. In such circumstances, atrio-ventricular delay may indicate block. For example, an atrio-ventricular delay of more than approximately 200 ms in a non-atrial paced heart may indicate some degree of block or conduction problem while an atrio-ventricular delay of more than approximately 250 ms in an atrial paced heart may indicate some degree of block or conduction problem.

As inferred in the Background section, significant asynchronous ventricular contraction (e.g., non-optimal VV delay) may in some instances impair cardiac function. Thus, where a patient has an interventricular delay that would result in significant asynchronous contraction, various exemplary methods, devices and/or systems described herein may treat such a cardiac condition and reduce deleterious effects associated with such the condition. Hence, various exemplary methods that pace in response to right and left ventricular conduction asymmetries may improve cardiac function.

FIG. 4 shows an approximate anatomical diagram of a heart and two sets of waveforms 400. One set of waveforms 410 corresponds in part to right ventricular activity while another set of waveforms 420 corresponds in part to left ventricular activity. Action potentials propagating through the heart are labeled as follows: 1, associated with a paced atrial stimulus and the atria; 2, associated with the atrio-ventricular node (AVN); and 3, associated with right and left bundle branches of the ventricles. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

The two sets of waveforms 410, 420 show various IEGMs of heart activity (e.g., polarization, depolarization, etc.) wherein atrial depolarization is represented as an "A wave" and ventricular depolarization is represented as an "R wave", or QRS complex. Both sets 410, 420 show an A wave followed by an AVN conduction delay (AVN) and a right ventricular R wave or QRS complex ($R_{RV}$) for the set 410 and a left ventricular R wave or QRS complex ($R_{LV}$) for the set 420. Often detection of an R wave or QRS complex relies on signal amplitude or signal derivative with respect to time. Further, many detection methods are capable of assigning a time to a detected R wave or QRS complex or assigning a time span to an A wave to R wave or QRS complex interval, which are shown in FIG. 4 as $AR_{RV}$ for the right ventricle and $AR_{LV}$ for the left ventricle. If $AR_{RV}$ and $AR_{LV}$ are approximately equal, then the right ventricle and the left ventricle contract in an approximately synchronous manner. However, if $AR_{RV}$ and $AR_{LV}$ differ substantially, e.g., $|\Delta|=|AR_{LV}-AR_{RV}|>5$ ms, then the right ventricle and left ventricle contract in an asynchronous manner. Depending on patient or other factors, the time could be set at some time other than 5 ms. The variable $|\Delta|$ is shown as the absolute value of the difference while herein and in the figures the variable $\Delta$ (e.g., $\Delta=AR_{LV}-AR_{RV}$) may be less than zero when $AR_{RV}$ exceeds $AR_{LV}$ or greater than zero when $AR_{LV}$ exceeds $AR_{RV}$.

To facilitate measurement of $AR_{RV}$ or $AR_{LV}$, in instances where ventricular pacing occurs, the AV delay (e.g., $AV_{RV}$ and/or $AV_{LV}$) may be increased to a value greater than the expected $AR_{RV}$ or $AR_{LV}$. Of course, where possible, ventricular pacing is optionally disabled, set to a back-up mode, etc.

Referring to FIG. 5, an approximate anatomical diagram of a heart and two sets of waveforms 500. One set of waveforms 510 corresponds to atrial and right ventricular activity and the other set of waveforms 520 corresponds to atrial and left ventricular activity. The two sets of waveforms approximate IEGM waveforms that may be sensed in vivo using an implanted device. In both sets 510, 520, A represents an atrial waveform based on an atrial pace and ER represents an evoked response (e.g., capture) based on a ventricular pace (labeled "$V_{RV}$" or "$V_{LV}$").

In FIG. 5, action potentials propagating through the heart are labeled as follows: 1, associated with a paced atrial stimulus or an intrinsic SAN stimulus and the atria; 2, associated with the atrio-ventricular node (AVN); and 3, associated with a paced right ventricle and a paced left ventricle. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3). However, ventricular pacing may override an atrial paced or intrinsic stimulus or may allow for ventricular stimulation and contraction where AVN conduction is impaired. Thus, in this example, ventricular rhythm typically relies on ventricular stimulation and conduction of electrical activity through the ventricles.

As mentioned, the two sets of waveforms of heart activity (e.g., polarization, depolarization, etc.) include atrial depolarization represented as an "A wave" and ventricular depolarization represented as an "ER wave" or evoked response. The delay between the atrial stimulus and the right ventricular stimulus is referred to as $AV_{RV}$ while the delay between the atrial stimulus and the left ventricular stimulus is referred to as $AV_{LV}$. The set 510 shows an A wave followed by an AVN conduction delay (AVN) and a right ventricular ER wave or evoked response. The set 520 shows an A wave followed by an AVN conduction delay (AVN) and a left ventricular evoked response ($ER_{LV}$). Often detection of an R wave or an evoked response relies on signal amplitude or signal derivative with respect to time. Further, many detection methods are capable of assigning a time to a detected R wave or evoked response or assigning a time span to an A wave to R wave or evoked response interval, which are shown in FIG. 5 as A-ER$_{RV}$ for the right ventricle and A-ER$_{LV}$ for the left ventricle. If A-ER$_{RV}$ and A-ER$_{LV}$ are approximately equal, then the right ventricle and the left ventricle contract in a substantially synchronous manner. While FIG. 5 shows a paced atrial stimulus, an intrinsic SAN stimulus may suffice and hence result in P-ER waveforms and corresponding P-ER$_{RV}$ and P-ER$_{LV}$ times. Information shown in FIG. 6 may be related to a scenario such as that shown in FIG. 5. In particular, where pacing occurs in both ventricles, corresponding IEGM waveforms may appear substantially the same as those of the set 510 and/or the set 520. Noting that, in general, an implanted device typically has a single atrial sensing channel and typically one or two ventricular channels (e.g., optionally one switchable channel that can switch between sensing in the left ventricle and the right ventricles and/or one ventricle and both ventricles).

Figure 6:
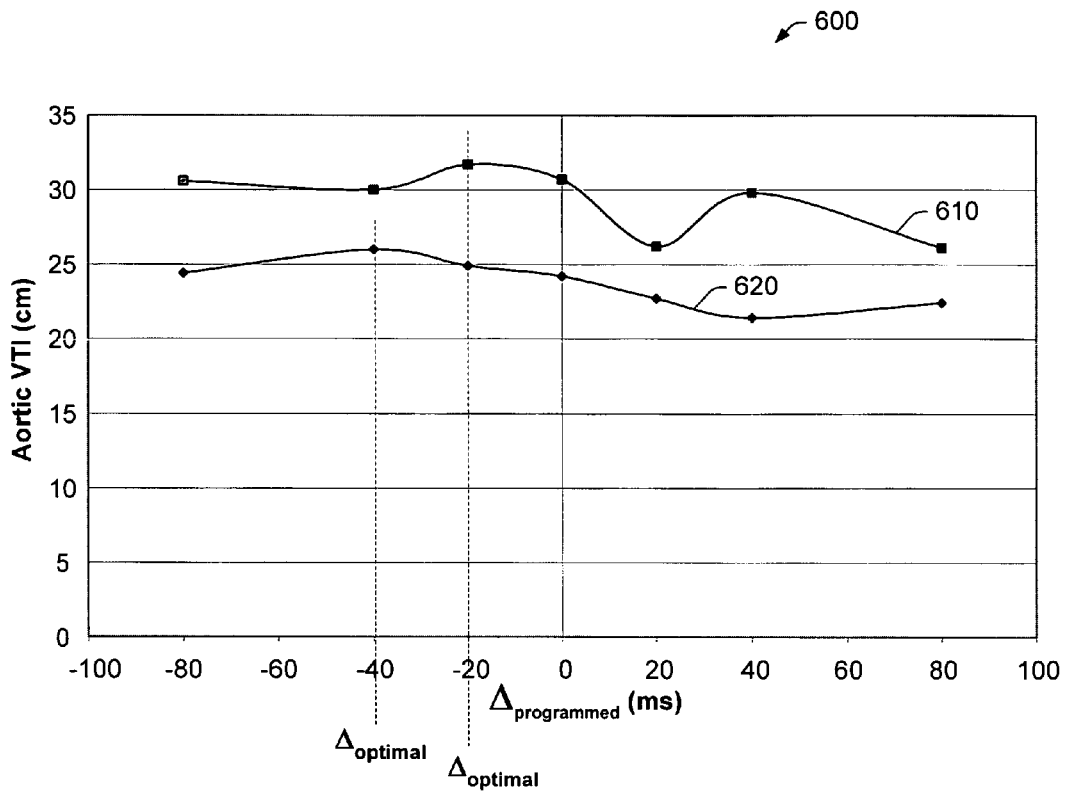
FIG. 6 is an exemplary plot of aortic velocity time integral versus a programmed interventricular conduction delay and exemplary equations for a parameter $\alpha$.

FIG. 6 shows a plot 600 of aortic velocity time integral versus $\Delta_{programmed}$ wherein, as shown, $\Delta_{programmed}$=AV$_{LV}$–AV$_{RV}$ or PV$_{LV}$–PV$_{RV}$. Thus, a $\Delta_{programmed}$ value less than zero indicates that for bi-ventricular pacing, a pacing stimulus or stimuli was delivered to the left ventricle prior to the right ventricle. A $\Delta_{programmed}$ of zero indicates that both AV$_{RV}$ and AV$_{LV}$ or PV$_{RV}$ and PV$_{LV}$ were set to approximately equal AV or PV times, which may optionally be an overall optimal time (e.g., AV$_{optimal}$ and PV$_{optimal}$).

The information of plot 600 was acquired using human subjects and echocardiograms. The velocity time integral, VTI, is the product of blood velocity in the aorta over a period of time. In general, the period of time corresponds to a beat-to-beat time and hence VTI typically correlates well with or serves as an indicator of cardiac performance. Thus, a higher VTI value normally indicates better cardiac performance.

The plot 600 includes data 610, 620 for two patients. As plotted, the upper data 610 exhibits a maximum VTI at a $\Delta_{programmed}$ of approximately –20 ms (e.g., left ventricular stimulus delivered 20 ms prior to the right ventricular stimulus) whereas the lower data 620 exhibits a maximum VTI at a $\Delta_{programmed}$ of approximately –40 ms (e.g., left ventricular stimulus delivered 40 ms prior to the right ventricular stimulus). Thus, the data 610, 620 indicate that, for these particular patients, cardiac performance is improved by pacing the left ventricle prior to the right ventricle. Further, for each patient, a corresponding optimal $\Delta_{programmed}$ exists, referred to herein as $\Delta_{optimal}$.

Referring again to FIG. 3 or 4, a comparison between $\Delta$ and $\Delta_{programmed}$ or $\Delta_{optimal}$ can indicate a difference between a current cardiac therapy or state and a potentially better cardiac therapy or state. For example, consider the following equation (Eqn. 1):

$$\alpha = \Delta_{optimal}/\Delta \quad (1)$$

where $\alpha$ is an optimization parameter. Hence in the example of FIG. 6, where the patient corresponding to data 610 had a $\Delta$ of approximately –40 ms and the patient corresponding to data 620 had a $\Delta$ of approximately –80 ms, the parameter $\alpha$ was approximately 0.5 for both patients. The use of such an optimization parameter is described further below. In general, the closer $\alpha$ is to unity, there may be little need to pace either ventricle if the PR$_{RV}$, PR$_{LV}$, AR$_{RV}$, and/or AR$_{LV}$ times are acceptable (noting that acceptable AR times are generally longer than acceptable PR times due to conduction differences between a paced atrial stimulus and intrinsic atrial activity).

While the information of FIG. 6 pertains primarily to ventricular activity, such an analysis may be performed for atrial activity. For example, where bi-atrial pacing is available, a programmed value for atrial activity may be defined as $\Delta_{programmed}$=A$_{LA}$–A$_{RA}$, wherein a negative value indicates that the right atrium was paced prior to the left atrium. An echocardiogram examination or other suitable examination may be used to determine an optimal value (e.g., $\Delta_{optimal}$=A$_{LA}$–A$_{RA}$). Yet further, an atrial parameter, or $\alpha_{atrial}$, may be used in an implantable device to adjust and/or determine one or more pacing times of one or both atria.

Some implantable devices allow left atrial pacing via an electrode on a lead positioned in the coronary sinus. For example, the exemplary device 100 includes the lead 106, which optionally has one or more electrodes positioned proximate to the left atrium and capable of delivering stimulation to the left atrium and/or sensing left atrial activity. Right atrial pacing and/or sensing may occur via, for example, the lead 104 and one or more electrodes, as appropriate. Yet further, one or more electrodes may be used to sense both right atrial and left atrial activity using one or more sensing channels. For example, a right atrial lead and a left atrial lead may connect to a single sensing channel to acquire a signal that includes indicia of right atrial activity and left atrial activity. Such an arrangement may allow for determination of an atrial $\Delta$ (e.g., P$_{LA}$–P$_{RA}$, A$_{LA}$–P$_{RA}$, P$_{LA}$–A$_{RA}$) and/or other parameters.

Figure 8:
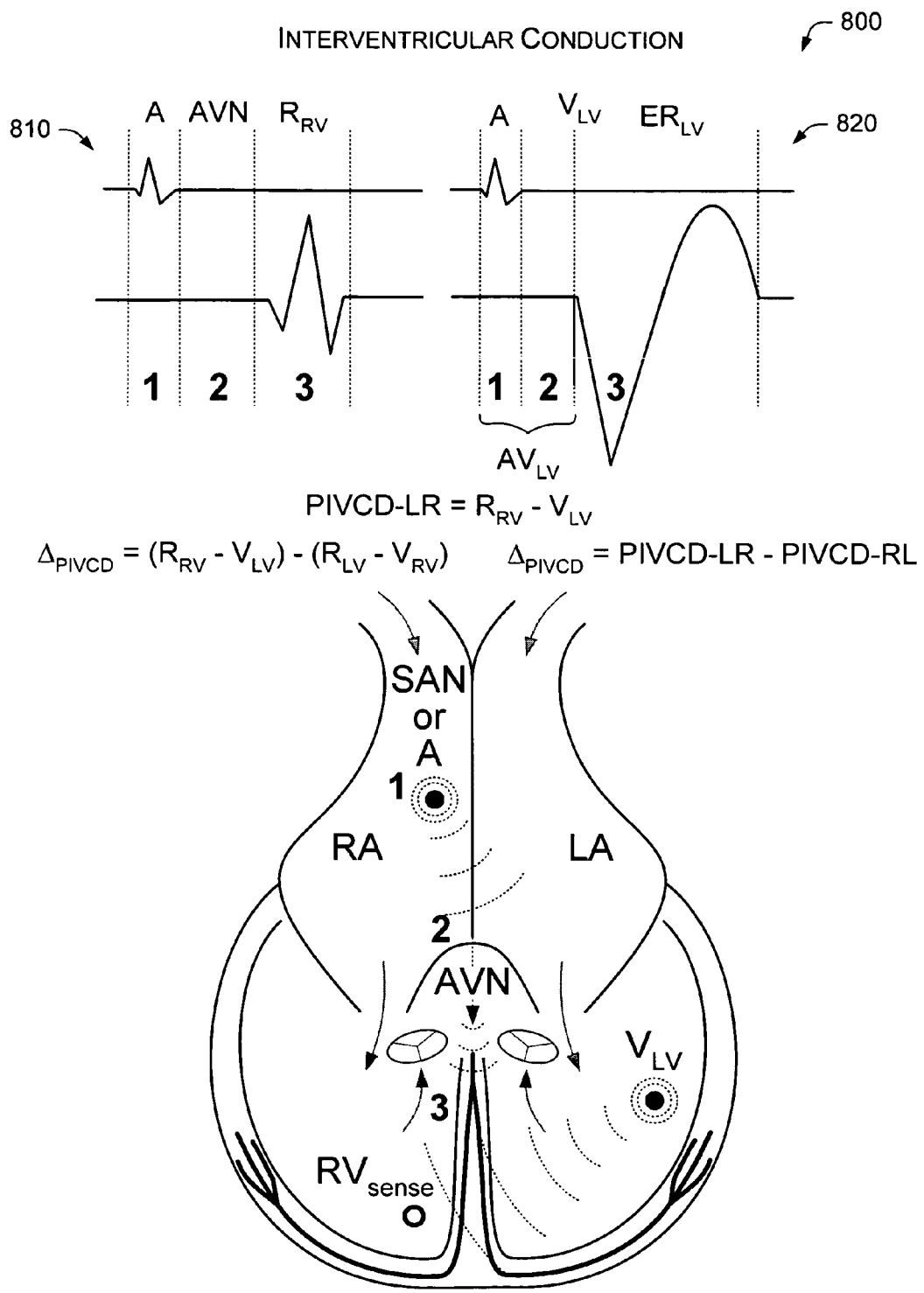
FIG. 8 is an approximate anatomical diagram of a heart and two sets of IEGM waveforms wherein one set includes an evoked response in a left ventricle and the other set includes a response from a conducted event in a right ventricle.

FIGS. 7 and 8 show plots, approximate anatomical diagrams and equations associated with yet another delay time, $\Delta_{PIVCD}$, referred to a paced interventricular conduction delay (PIVCD). FIG. 7 pertains to pacing in a right ventricle and sensing in a left ventricle wherein the time between pacing and sensing is referred to as a right to left PIVCD or PIVCD-RL, which equals R$_{LV}$–V$_{RV}$, wherein V$_{RV}$ is a pace time of a pacing stimulus in the right ventricle and R$_{LV}$ is a sense time of a right ventricle, evoked response wavefront in the left ventricle due to the paced stimulus in the right ventricle. Thus, PIVCD-RL is normally greater than zero. To ensure that the pacing stimulus in the right ventricle results in an evoked response, a capture routine or algorithm may be implemented. Thus, various exemplary methods, devices and/or systems include a capture algorithm (e.g., autocapture).

FIG. 7 shows a set of waveforms 710 that include an atrial event (e.g., A or P), an atrial to ventricular paced delay AV$_{RV}$, a ventricular pace time V$_{RV}$ and a sensed evoked response in the right ventricle ER$_{RV}$. Another set of waveforms 720 pertains primarily to the left ventricle and includes an atrial event (e.g., A or P), an AVN delay and a sensed evoked response in the left ventricle R$_{LV}$ which is a result of the stimulus V$_{RV}$ in the right ventricle. To ensure that the sensed evoked response in the left ventricle R$_{LV}$ is not due to conducted electrical activity from the atria, a sufficiently short ventricular paced delay AV$_{RV}$ is used. For example, a paced delay AV$_{RV}$ of approximately 30 ms to approximately 70 ms may suffice. In one example, AV$_{RV}$ is set to approximately 50 ms to approximately 80 ms. AV$_{RV}$ may also be set sufficiently short to avoid fusion. While AV is referred to, PV may also apply where appropriate.

In general, bipolar sensing (or other multipolar/combipolar sensing) may increase signal to noise of the sensed activation in the left ventricle when compared to unipolar sensing that includes use of an in vivo, yet non-local electrode such as a pulse generator can. The latter technique is more often used in detection of evoked response or applications utilizing far-field signals. Further, bipolar sensing that includes two electrodes positioned in proximity to each other (e.g., less than approximately 4 cm), may increase signal to noise and sensitivity and better sense timing of an activation wave front proximate to the electrodes.

FIG. 8 pertains to pacing in a left ventricle and sensing in a right ventricle wherein the time between pacing and sensing is referred to as a left to right PIVCD or PIVCD-LR, which equals $R_{RV}-V_{LV}$, wherein $V_{LV}$ is a pace time of a pacing stimulus in the left ventricle and $R_{RV}$ is a sense time of a left ventricle, evoked response wavefront in the right ventricle due to the paced stimulus in the left ventricle. Thus, PIVCD-LR is normally greater than zero. To ensure that the pacing stimulus in the left ventricle results in an evoked response, a capture routine or algorithm may be implemented. Thus, various exemplary methods, devices and/or systems include a capture algorithm (e.g., autocapture).

FIG. 8 shows a set of waveforms 820 that includes an atrial event (e.g., A or P), an atrial to ventricular paced delay $AV_{LV}$, a ventricular pace time $V_{LV}$ and a sensed evoked response in the left ventricle $ER_{LV}$. Another set of waveforms 810 pertains primarily to the right ventricle and includes an atrial event (e.g., A or P), an AVN delay and a sensed evoked response in the right ventricle $R_{RV}$ which is a result of the stimulus $V_{LV}$ in the left ventricle. To ensure that the sensed evoked response in the right ventricle $R_{RV}$ is not due to conducted electrical activity from the atria, a sufficiently short ventricular paced delay $AV_{LV}$ is used. For example, a paced delay $AV_{LV}$ of approximately 30 ms to approximately 70 ms may suffice. In one example, $AV_{LV}$ is set to approximately 50 ms to approximately 80 ms. $AV_{LV}$ may also be set sufficiently short to avoid fusion. While AV is referred to, PV may also apply where appropriate.

In general, bipolar sensing (or other multipolar/combipolar sensing) may increase signal to noise of the sensed activation response in the left ventricle when compared to unipolar sensing that includes use of an in vivo, yet non-local electrode such as a pulse generator can. The latter technique is often more used in detection of evoked response or the applications utilizing far-field signals. Further, bipolar sensing that includes two electrodes positioned in proximity to each other (e.g., less than approximately 4 cm), may increase signal to noise and sensitivity and better localize an activation wavefront.

Thus, in summary, FIG. 3 through FIG. 8 described the following delays that are related to pacing in the right ventricle and/or the left ventricle:

| | |
|---|---|
| PV | Delay between an atrial event and a paced ventricular event |
| $PV_{optimal}$ | Optimal PV delay |
| $PV_{RV}$ | PV delay for right ventricle |
| $PV_{LV}$ | PV delay for left ventricle |
| AV | Delay for a paced atrial event and a paced ventricular event |
| $AV_{optimal}$ | Optimal AV delay |
| $AV_{RV}$ | AV delay for right ventricle |
| $AV_{LV}$ | AV delay for left ventricle |
| $\Delta$ | Estimated interventricular delay, e.g., via IEGM, etc. |
| $\Delta_{programmed}$ | Programmed interventricular delay (e.g., a programmed VV delay) |
| $\Delta_{optimal}$ | Optimal interventricular delay, e.g., via hemodynamic sensing/sensor or other cardiac sensing |
| PIVCD-RL | Delay between paced RV and sensed LV |
| PIVCD-LR | Delay between paced LV and sensed RV |
| $\Delta_{PIVCD}$ | Paced interventricular conduction delay |

FIG. 9 shows various exemplary scenarios wherein at least some delay information is known. In these scenarios, delay information pertains to delay between an atrial event (e.g., A or P) and a sensed ventricular event (e.g., R). Thus, such delay information pertains to conduction from the atrium (or atria) to the right ventricle and/or the left ventricle.

In a first scenario, Scenario I, delay information, $AR_{LV}$ and/or $AR_{RV}$ (or $PR_{LV}$ and/or $PR_{RV}$), is assessed relative to a predetermined delay, $AR_{max}$ (or $PR_{max}$). As already mentioned, $AR_{max}$ or $PR_{max}$ may be approximately 250 ms or approximately 200 ms, respectively. Other values may be suitable depending on patient or other circumstances. In Scenario I, if one of the delays exceeds the predetermined delay, then pacing should occur in the ventricle associated with the delay that exceeds the predetermined delay. This ventricle is referred to herein as the master ventricle. For example, if $AR_{max}$ is 250 ms, $AR_{RV}$ is 150 ms and $AR_{LV}$ is 300 ms, then pacing should occur in the left ventricle because $AR_{LV}$ is greater than 250 ms.

In a second scenario, Scenario II, delay information, $AR_{LV}$ and $AR_{RV}$ (or $PR_{LV}$ and $PR_{RV}$), is assessed relative to a predetermined delay, $AR_{max}$ (or $PR_{max}$). In Scenario II, if both of the delays exceed the predetermined delay, then pacing should occur in both ventricles and first in the ventricle associated with the longest delay, which ventricle is referred to herein as the master ventricle. For example, if $PR_{max}$ is 200 ms, $PR_{RV}$ is 250 ms and $PR_{LV}$ is 300 ms, then pacing should occur both ventricles and first in the left ventricle because $PR_{LV}$ is greater than $PR_{RV}$.

In a third scenario, Scenario II, delay information, $AR_{LV}$ and $AR_{RV}$ (or $PR_{LV}$ and $PR_{RV}$), is assessed relative to a predetermined delay, $AR_{max}$ (or $PR_{max}$). In Scenario II, if both of the delays do not exceed the predetermined delay, then ventricular pacing may or may not occur depending on one or more other circumstances. For example, if $AR_{max}$ is 250 ms, $AR_{RV}$ is 150 ms and $AR_{LV}$ is 200 ms, then pacing may not occur because intrinsic conduction is apparently adequate. However, if the difference between $AR_{RV}$ and $AR_{LV}$ is deemed excessive or otherwise undesirable, then single or biventricular pacing may occur in an effort to compensate or correct for this difference.

FIG. 10 shows various, more specific examples related to Scenario I of FIG. 9, wherein at least some delay information is known about paced interventricular conduction delay (PIVCD). In these scenarios, such delay information pertains to delay between a paced event (e.g., V) in one ventricle and a sensed event (e.g., R) in another ventricle. Thus, such delay information pertains to conduction between the right ventricle and the left ventricle.

The more specific examples rely on a comparison between $|\Delta_{PIVCD}|$ and a PIVCD conduction related parameter $\epsilon$. The parameter $\epsilon$ represents an interventricular conduction limit for conduction between the ventricles and may represent a tolerable limit for conduction heterogeneity. For example, a large $\epsilon$ may be used to tolerate or to not compensate for conduction in one direction being significantly greater than conduction in the other direction.

As shown in FIG. 10, if $AR_{LV}$ is greater than $AR_{max}$ (or $PR_{LV}$ is greater than $PR_{max}$) and $|\Delta_{PIVCD}|$ is less than $\epsilon$, then pacing occurs in the left ventricle wherein the timing of the paced stimulus (or stimuli) follows the equation (Eqn. 2):

$$AV_{LV}=AV_{optimal}-|\Delta| \text{ or } PV_{LV}=PV_{optimal}-|\Delta| \qquad (2)$$

In Eqn. 2, $AV_{optimal}$ or $PV_{optimal}$ represents an optimal or predetermined delay. Thus, Eqn. 2 ensures that pacing compensates for at least some of the conduction problem associated with the left ventricle. If however, $|\Delta_{PIVCD}|$ is greater than or equal to $\epsilon$, then pacing occurs in the left ventricle wherein the timing of the paced stimulus (or stimuli) follows the equation (Eqn. 3):

$$AV_{LV}=AV_{optimal}-|\Delta|+\Delta_{PIVCD}) \text{ or}$$

$$PV_{LV}=PV_{optimal}-|\Delta|+\Delta_{PIVCD}) \quad (3)$$

Thus, Eqn. 3 ensures that pacing compensates for at least some of the conduction problem associated with the left ventricle and for at least some of the conduction problem associated with conduction between ventricles.

Consider a situation where $AR_{max}$ is 250 ms, $AR_{LV}$ is 300 ms, $AR_{RV}$ is 210 ms, $AV_{optimal}$ is 180 ms, $\epsilon$ is 5 ms, PIVCD-LR is 10 ms and PIVCD-RL is 20 ms (better left to right or poorer right to left conduction). In this situation, $|\Delta|$ is |300 ms−210 ms| or 90 ms and $\Delta_{PIVCD}$ is (10 ms−20 ms) or −10 ms. Thus, pacing should occur in the left ventricle with an atrio-ventricular delay as follows:

$$AV_{LV}=180 \text{ ms}-(90 \text{ ms}+(-10 \text{ ms}))=100 \text{ ms}$$

In this example, if $AR_{RV}$ is 210 ms, then the difference between ventricular activation is approximately 210 ms−100 ms or 110 ms, wherein the left ventricle is activated prior to the right ventricle, which may be referred to as $|\Delta_{actual}|$ which is equal to $|AV_{LV}-AR_{RV}|$.

As shown in FIG. 10, if $AR_{RV}$ is greater than $AR_{max}$ (or $PR_{RV}$ is greater than $PR_{max}$) and $|\Delta_{PIVCD}|$ is less than $\epsilon$, then pacing occurs in the right ventricle wherein the timing of the paced stimulus (or stimuli) follows the equation (Eqn. 4):

$$AV_{RV}=AV_{optimal}-|\Delta| \text{ or } PV_{RV}=PV_{optimal}-|\Delta| \quad (4)$$

In Eqn. 4, $AV_{optimal}$ or $PV_{optimal}$ represents an optimal or predetermined delay. Thus, Eqn. 4 ensures that pacing compensates for at least some of the conduction problem associated with the right ventricle. If however, $|\Delta_{PIVCD}|$ is greater than or equal to $\epsilon$, then pacing occurs in the right ventricle wherein the timing of the paced stimulus (or stimuli) follows the equation (Eqn. 5):

$$AV_{RV}=AV_{optimal}-|\Delta|-\Delta_{PIVCD}) \text{ or}$$

$$PV_{RV}=PV_{optimal}-|\Delta|-\Delta_{PIVCD}) \quad (5)$$

Thus, Eqn. 5 ensures that pacing compensates for at least some of the conduction problem associated with the right ventricle and for at least some of the conduction problem associated with conduction between ventricles.

Consider a situation where $AR_{max}$ is 250 ms, $AR_{RV}$ is 280 ms, $AR_{LV}$ is 230 ms, $AV_{optimal}$ is 190 ms, $\epsilon$ is 5 ms, PIVCD-LR is 10 ms and PIVCD-RL is 20 ms (better left to right or poorer right to left conduction). In this situation, $|\Delta|$ is |230 ms−280 ms| or 50 ms and $\Delta_{PIVCD}$ is (10 ms−20 ms) or −10 ms. Thus, pacing should occur in the right ventricle with an atrio-ventricular delay as follows:

$$AV_{RV}=190 \text{ ms}-(50 \text{ ms}-(-10 \text{ ms}))=130 \text{ ms}$$

In this situation, the calculated delay of the pacing stimulus (or stimuli) in the right ventricle accounts for conduction issues from the atria to the ventricles and for poor right to left interventricular conduction. Further in this example, if $AR_{LV}$ is 230 ms, then the difference between ventricular activation is approximately 230 ms−130 ms or 100 ms, wherein the right ventricle is activated prior to the left ventricle, which may be referred to as $|\Delta_{actual}|$ which is equal to $|AR_{LV}-AV_{RV}|$.

FIG. 11 shows various, more specific examples related to Scenario II of FIG. 9, wherein at least some delay information is known about paced interventricular conduction delay (PIVCD). In these scenarios, such delay information pertains to delay between a paced event (e.g., V) in one ventricle and a sensed event (e.g., R) in another ventricle. Thus, such delay information pertains to conduction between the right ventricle and the left ventricle.

The more specific examples rely on a comparison between $|\Delta_{PIVCD}|$ and a PIVCD conduction related parameter $\epsilon$. The parameter $\epsilon$ represents an interventricular conduction limit for conduction between the ventricles and may represent a tolerable limit for conduction heterogeneity. For example, a large $\epsilon$ may be used to tolerate or to not compensate for conduction in one direction being significantly greater than conduction in the other direction.

As shown in FIG. 11, if $AR_{LV}$ and $AR_{RV}$ are greater than $AR_{max}$ (or $PR_{LV}$ and $PR_{RV}$ are greater than $PR_{max}$), $AR_{LV}$ is greater than $AR_{RV}$ and $|\Delta_{PIVCD}|$ is less than $\epsilon$, then pacing occurs in both ventricles wherein $AV_{RV}$ is set to $AV_{optimal}$ and in the left ventricle the timing of the paced stimulus (or stimuli) follows the equation (Eqn. 6):

$$AV_{LV}=AV_{RV}-|\Delta| \text{ or } PV_{LV}=PV_{RV}-|\Delta| \quad (6)$$

Thus, Eqn. 6 ensures that pacing compensates for at least some of the conduction problem associated with the left ventricle. If however, $|\Delta_{PIVCD}|$ is greater than or equal to $\epsilon$, then $AV_{RV}$ is set to $AV_{optimal}$ and pacing occurs in the left ventricle wherein the timing of the paced stimulus (or stimuli) follows the equation (Eqn. 7):

$$AV_{LV}=AV_{RV}-(|\Delta|+\Delta_{PIVCD}) \text{ or}$$

$$PV_{LV}=PV_{RV}-(|\Delta|+\Delta_{PIVCD}) \quad (7)$$

Thus, Eqn. 7 ensures that pacing compensates for at least some of the conduction problem associated with the left ventricle and for at least some of the conduction problem associated with conduction between ventricles.

Consider a situation where $AR_{max}$ is 250 ms, $AR_{LV}$ is 300 ms, $AR_{RV}$ is 260 ms, $AV_{optimal}$ is 180 ms, $\epsilon$ is 5 ms, PIVCD-LR is 10 ms and PIVCD-RL is 20 ms (better left to right or poorer right to left conduction). In this situation, $|\Delta|$ is |300 ms−260 ms| or 40 ms and $\Delta_{PIVCD}$ is (10 ms−20 ms) or −10 ms. Thus, pacing should occur in the left ventricle with an atrio-ventricular delay as follows:

$$AV_{LV}=180 \text{ ms}-(40 \text{ ms}+(-10 \text{ ms}))=150 \text{ ms}$$

In this example, if $AV_{RV}$ is 180 ms, then the difference between ventricular activation is approximately 180 ms−150 ms or 30 ms, wherein the left ventricle is activated prior to the right ventricle, which may be referred to as $\Delta_{actual}$ which is equal to $|AV_{LV}-AV_{RV}|$.

As shown in FIG. 11, if $AR_{RV}$ and $AR_{LV}$ are greater than $AR_{max}$ (or $PR_{RV}$ and $PR_{LV}$ are greater than $PR_{max}$), $AR_{RV}$ is greater than $AR_{LV}$ and $|\Delta_{PIVCD}|$ is less than $\epsilon$, then $AV_{LV}$ is set to $AV_{optimal}$ and pacing occurs in the right ventricle wherein the timing of the paced stimulus (or stimuli) follows the equation (Eqn. 8):

$$AV_{RV}=AV_{LV}-|\Delta| \text{ or } PV_{RV}=PV_{LV}-|\Delta| \quad (8)$$

Thus, Eqn. 8 ensures that pacing compensates for at least some of the conduction problem associated with the right ventricle. If however, $|\Delta_{PIVCD}|$ is greater than or equal to $\epsilon$, then $AV_{LV}$ is set to $AV_{optimal}$ and pacing occurs in the right ventricle wherein the timing of the paced stimulus (or stimuli) follows the equation (Eqn. 9):

$$AV_{RV}=AV_{LV}-(|\Delta|-\Delta_{PIVCD}) \text{ or}$$

$$PV_{RV}=PV_{LV}-(|\Delta|-\Delta_{PIVCD}) \quad (9)$$

Thus, Eqn. 9 ensures that pacing compensates for at least some of the conduction problem associated with the right ventricle and for at least some of the conduction problem associated with conduction between ventricles.

Consider a situation where $AR_{max}$ is 250 ms, $AR_{RV}$ is 280 ms, $AR_{LV}$ is 270 ms, $AV_{optimal}$ is 190 ms, $\epsilon$ is 5 ms, PIVCD-LR is 10 ms and PIVCD-RL is 20 ms (better left to right or poorer right to left conduction). In this situation, $|\Delta|$ is |270 ms−280 ms| or 10 ms and $\Delta_{PIVCD}$ is (10 ms−20 ms) or −10 ms. Thus, pacing should occur in the right ventricle with an atrio-ventricular delay as follows:

$$AV_{RV}=190\ ms-(10\ ms-(-10\ ms))=170\ ms$$

In this situation, the calculated delay of the pacing stimulus (or stimuli) in the right ventricle accounts for conduction issues from the atria to the ventricles and for poor right to left interventricular conduction. Further in this example, because $AV_{LV}$ is 190 ms, the difference between ventricular activation is approximately 190 ms−170 ms or 20 ms, wherein the right ventricle is activated prior to the left ventricle, which may be referred to as $|\Delta_{actual}|$ which is equal to $|AV_{LV}-AV_{RV}|$.

In the foregoing examples of FIG. 10 and FIG. 11, there is no explicit compensation based on the information shown in the plot 600 of FIG. 6. For example, the exemplary parameter $\alpha$ (e.g., $\alpha = \Delta_{optimal}/\Delta$) does not appear in Eqns. 2 through 9. FIG. 12 exhibits how the parameter $\alpha$ may be used to further enhance cardiac performance in Scenario I and/or Scenario II. In general, the examples of FIG. 12 use an optimal AV delay and use the parameter $\alpha$ to arrive at an optimal interventricular delay.

For $AR_{RV} > AR_{LV}$ (or $PR_{RV} > PR_{LV}$) and pacing in a single ventricle (e.g., Scenario I), the following equation (Eqn. 10) may be used to determine an appropriate $AV_{RV}$:

$$AV_{RV}=AV_{optimal}-\alpha|\Delta|\ or\ PV_{RV}=PV_{optimal}-\alpha|\Delta| \quad (10)$$

In Eqn. 10 the term $\alpha|\Delta|$ equals or approximates $\Delta_{optimal}$. Thus, a patient's device may deliver therapy using an optimal atrio-ventricular delay in one chamber together with an optimal interventricular delay.

In instances where $\Delta_{PIVCD}$ information is available and an adjustment for interventricular conduction desirable, then the following equation (Eqn. 11) may be used in Scenario I where $AR_{LV} > AR_{RV}$ (or $PR_{LV} > PR_{RV}$):

$$AV_{LV}=AV_{optimal}-\alpha(|\Delta|+\Delta_{PIVCD})\ or$$

$$PV_{LV}=PV_{optimal}-\alpha(|\Delta|+\Delta_{PIVCD}) \quad (11)$$

For Scenario I where $AR_{RV} > AR_{LV}$ (or $PR_{RV} > PR_{LV}$), the sign of the paced interventricular conduction delay time is switched from "+" to "−", where $\Delta_{PIVCD}$ is defined as PIVCD-LR−PIVCD-RL. Similar equations exist for Scenario II, wherein the parameter $\alpha$ is used to adjust $\Delta$ or the term $|\Delta|+/-\Delta_{PIVCD}$.

While the parameter $\alpha$ was described with respect to echocardiogram data, other techniques may be suitable to determine such a parameter. As already mentioned, the parameter $\alpha$ may depend on or be adjusted based wholly, or in part, on IEGM information acquired in vivo using traditional sensing leads, electrodes and circuitry. Further, a patient may have more than one such parameter. For example, a patient may have an $\alpha_{sleep}$, an $\alpha_{exercise}$, an $\alpha_{normal}$, etc., depending on conditions or states the patient is likely to experience. In such a manner, a detector may detect a condition or state and then select a corresponding $\alpha$. Parameters and/or parameter selection may be based on cardiac information such as QRS and conduction times. For example, if a patient exhibits normal $PR_{RV}$ conduction, a QRS less than approximately 150 ms and excessive $PR_{LV}$ conduction, then a may be set to 0.5 or other value as appropriate. Various sensors are mentioned above with respect to the exemplary device 100 of FIG. 2. Such sensors may provide information for use in determining an $\alpha$ parameter or other parameters suitable for use in adjusting pacing variables.

Various information pertaining to conduction is optionally used to determine, estimate and/or update an optimal atrio-ventricular delay (e.g., $AV_{optimal}$ or $PV_{optimal}$). For example, if $AR_{RV} < AR_{LV}$ or $PR_{RV} < PR_{LV}$, a new optimal atrio-ventricular delay may be determined using the following equation (Eqn. 12):

$$AV_{optimal}(n+1)=AV_{optimal}(n)*(AR_{RV}(n+1)/AR_{RV}(n))$$
or
$$AV_{optimal}(n+1)=AV_{optimal}(n)*(PR_{RV}(n+1)/PR_{RV}(n)) \quad (12)$$

If $AR_{LV} < AR_{RV}$ or $PR_{LV} < PR_{RV}$, then $AR_{LV}$ or $PR_{LV}$ could be used to update $AV_{optimal}$. For example, if $AR_{LV}(n+1)$ is 160 ms, $AR_{RV}(n+1)$ is 210 ms, $AV_{optimal}(n)$ is 150 ms and $AR_{LV}(n)$ is 170 ms, then $AV_{optimal}(n+1)$ is approximately 150 ms*(160 ms/170 ms) or 141 ms.

Updating of information such as an $AV_{optimal}$ delay may occur based on a schedule, a number of beats, a change in cardiac condition, etc. For example, if a change of more than 10% occurs in the shorter atrio-ventricular conduction delays over a 1 hour period, then $AV_{optimal}$ is updated. Of course, updating may occur upon a session with a caretaker wherein information is obtained and used to determine $AV_{optimal}$. Further, an exemplary implanted device optionally stores changes in $AV_{optimal}$ which may be subsequently used by a caretaker, for example, to improve therapy, to diagnose cardiac condition, etc.

Various exemplary methods described herein are optionally implemented using an implantable device having a single sensing channel for one or more electrodes positioned in or on the right ventricle and for one or more electrodes positioned in or on the left ventricle. In such devices, switching is optionally used to switch between sensing of the right ventricle and the left ventricle. Alternatively, both ventricles are sensed at the same time wherein an algorithm or other detection method is used to distinguish at least some information associated with the right ventricle from at least some information associated with the left ventricle.

Figure 13:
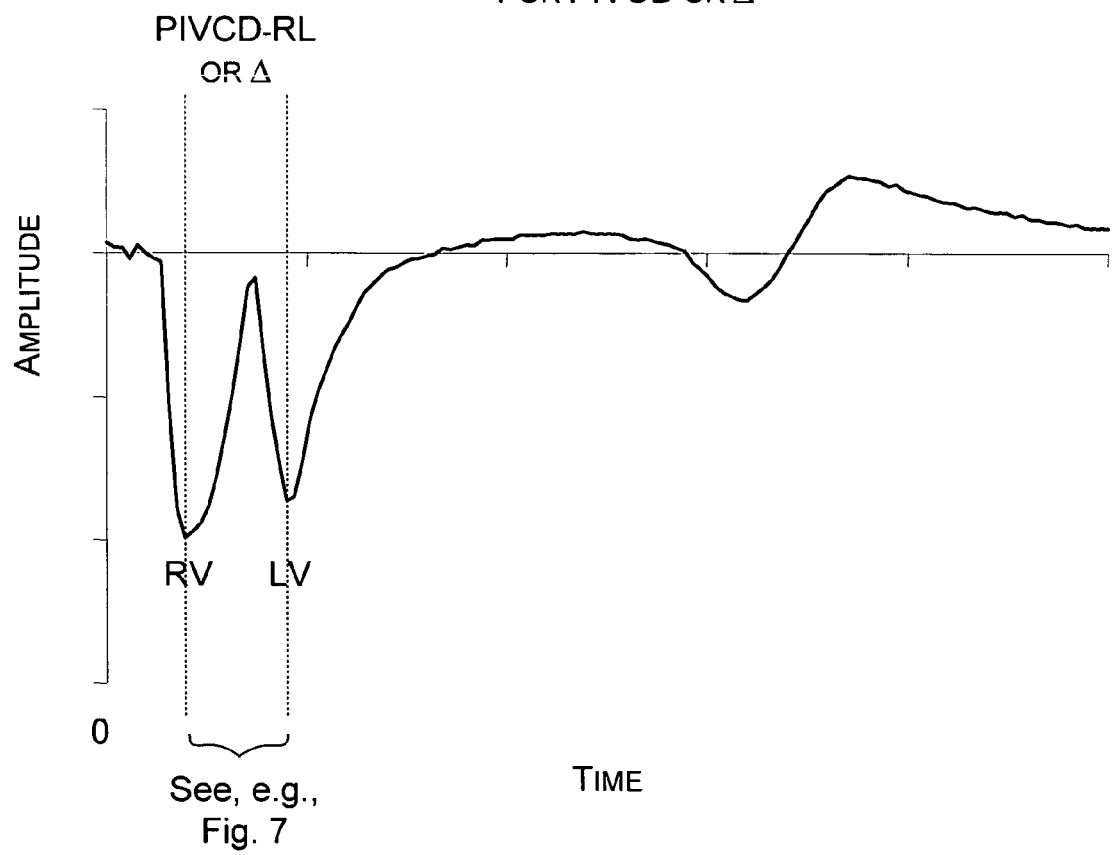
FIG. 13 is an exemplary IEGM plot acquired in a study using a unipolar sensing arrangement for a right ventricular tip electrode and a left ventricular tip electrode having a common electrode.

FIG. 13 shows an exemplary IEGM plot 1300 acquired in a study using a unipolar sensing arrangement for a right ventricular tip electrode and a left ventricular tip electrode having a common electrode (e.g., can, device sensing circuit, etc.). In this unipolar arrangement, an electrical connection exists between right and left ventricular sensing circuits. In particular, depolarization due to atrio-ventricular intrinsic conduction was sensed at the right ventricle and then sensed at the left ventricle as the activation propagated to the left ventricle. In this example, the peak-to-peak time delay typically approximates $\Delta$. However, it may approximate PIVCD-RL in the case of FIGS. 7 and 8. If RV is paced at a short AV delay, the time delay from pacing RV to the peak of the conduction to the left ventricle approximates PIVCD-RL. In an alternative example, not shown in FIG. 13, a pacing stimulus was delivered to the right ventricle at a time of approximately 0 ms. This pacing stimulus resulted in capture of the right ventricle and the IEGM showed a corresponding right ventricular evoked response. In this example, the left ventricle was not paced or initially captured by the pace to the right ventricle but after a short delay, the left ventricle depolarized spontaneously due to conduction of the paced event from the right ventricle. Hence, the delay between the right ventricular peak (RV) and the left ventricular peak (LV) approximates a paced interventricular conduction delay from right ventricle to left ventricle (see, e.g., PIVCD-RL of FIG. 7). Thus, the plot 1300 helps to demonstrate a particular exemplary manner in which an implantable device that uses a single sensing amplifier for right and left ventricular sensing channels can determine paced interventricular conduction delay and thus, $\Delta_{PIVCD}$. In addition, such a sensing arrangement may be used to determine a VV delay (e.g., $\Delta$, etc.) based on an intrinsic or a paced atrial event that is then conducted to the left ventricle and the right ventricle.

Further, some implantable devices having sensing and pacing capabilities can deliver a stimulus to one ventricle and then switch to sensing of both ventricles. For example, in the plot 1300, the RV stimulus may have been delivered in an open configuration (e.g., RV and LV leads/electrodes not "connected") and, thereafter, leads/electrodes "shorted" to allow for sensing from both ventricles. Of course, where appropriate, pacing in one ventricle and sensing in the other ventricle may occur according to various arrangements.

Figure 14:
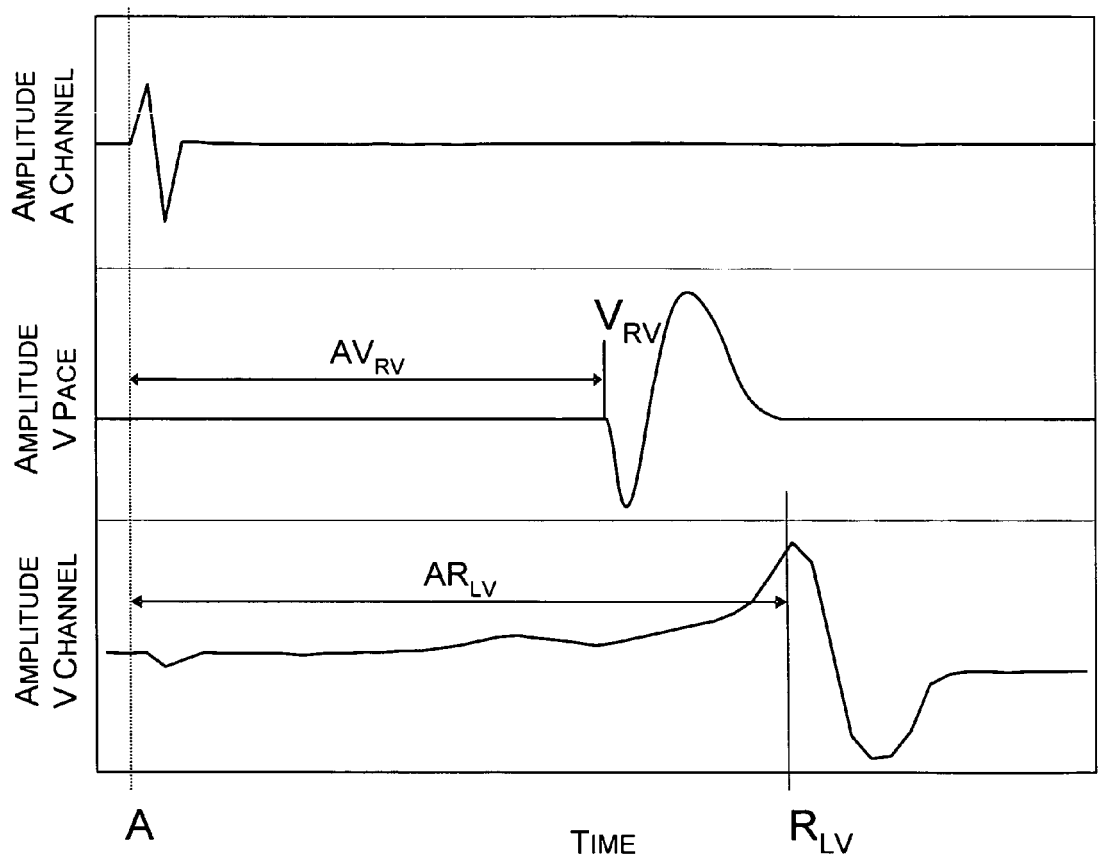
FIG. 14 is an exemplary atrial and ventricular IEGM plot acquired in a study using an implantable device optionally including a switchable channel for RV and LV sensing and/or pacing.

FIG. 14 shows an exemplary IEGM plot 1400 wherein the ventricular IEGM was acquired in a study using an implantable device including switchable channel for RV and LV sensing. Such a device may allow for measurement of $AR_{RV}/PR_{RV}$ and $AR_{LV}/PR_{LV}$ by switching between RV sensing to LV sensing. Accordingly, $\Delta$ may be ascertained. Such a device may also allow for pacing in the right ventricle and/or left ventricle. Further, such a device may ascertain PIVCD-RL and/or PIVCD-LR and optionally $\Delta_{PIVCD}$. For example, if an $AV_{RV}$ or $PV_{RV}$ delay is set short enough to avoid fusion, then $AR_{LV}$ or $PR_{LV}$ may be determined on the basis of LV sensing wherein the LV sensing sense electrical activity in the left ventricle (e.g., $R_{LV}$) stemming from the right ventricular stimulus (e.g., $V_{RV}$). In this example, PIVCD-RL may equal $AR_{LV}-AV_{RV}$ or $PR_{LV}-PV_{RV}$.

Other implantable devices may include RV and LV sensing channels that can operate at the same time. Such devices may allow for measurement of $AR_{RV}/PR_{RV}$ and $AR_{LV}/PR_{LV}$ on a beat-by-beat basis. For example, for a single beat, an atrial to right ventricular delay and an atrial to left ventricular delay may be ascertained. Such an exemplary method can reduce measurement error by determining such variable for a single beat as compared to determining one variable for one beat and another variable for a different beat. Detection of an event may be based on sensitivity programmed in devices or a criterion such as an amplitude value greater than approximately 40% of an expected QRS amplitude value.

Various exemplary methods, devices and/or systems may help to avoid cross ventricular sensing. For example, if an interventricular delay is less than interventricular conduction (e.g., PIVCD-RL and PIVCD-LR), the incidence of sensing paced ventricular events in an alert interval is reduced. Further, this incidence may be further reduced through use of an automatic capture algorithm.

Figure 15:
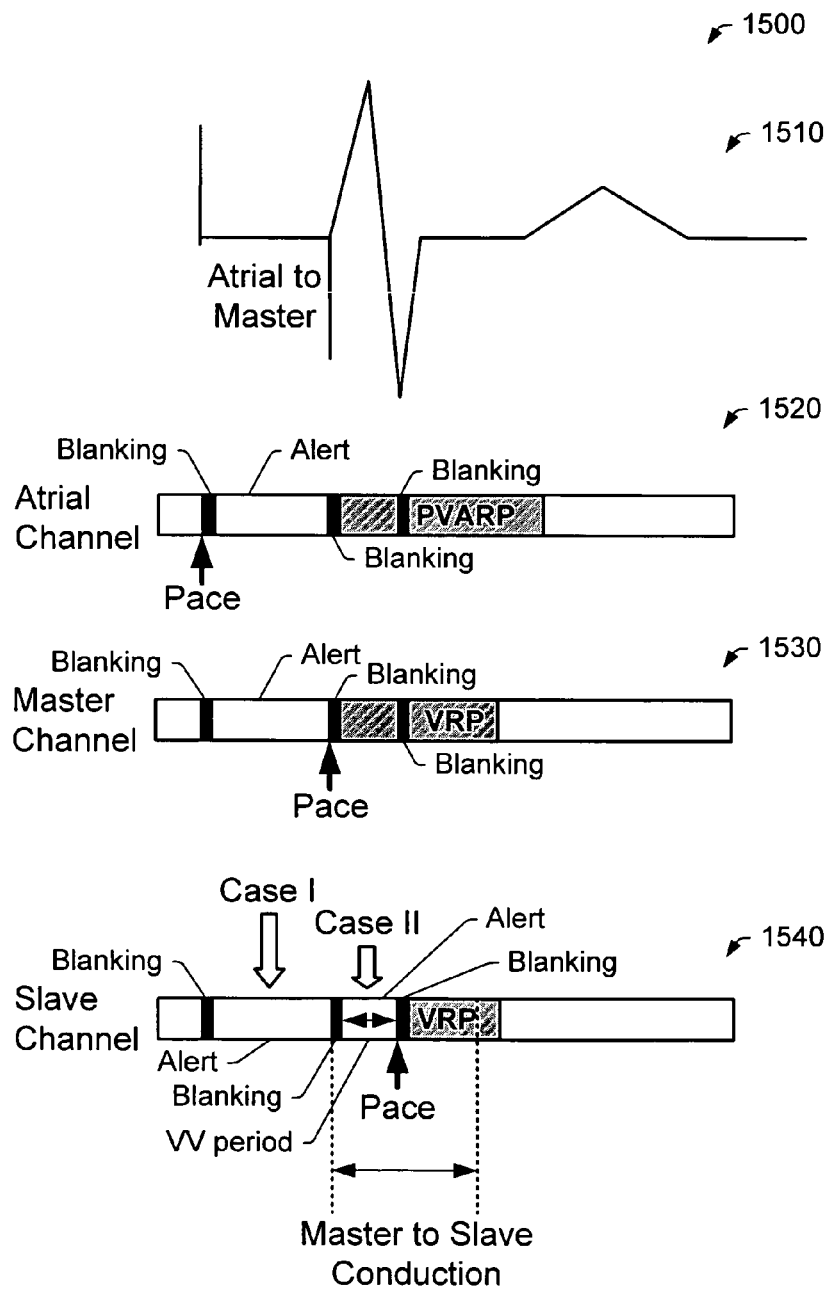
FIG. 15 is an exemplary scheme for triggering and/or inhibiting stimulation in response to sensing of intrinsic activity.

FIG. 15 shows an exemplary scheme 1500 wherein several cases exist for sensing an intrinsic or non-paced event. A waveform 1510 shows an atrial pace, a ventricular pace and a corresponding ventricular waveform (e.g., for a single ventricular sensing channel). An atrial channel 1520 includes various events including an atrial pace event. As shown, the atrial channel 1520 includes an atrial pace blanking period, an alert period, a first ventricular blanking period (e.g., a master ventricle blanking period), a post ventricular atrial refractory period (PVARP), and a second ventricular blanking period (e.g., a slave ventricle blanking period). Some of these periods are optional, depending, for example, on one or more sensed and/or programmed events.

The exemplary scheme 1500 also includes a master ventricular channel 1530. The master ventricular channel 1530 includes an atrial blanking period, an alert period, a master ventricle pace event, a master ventricle blanking period, a ventricular refractory period (VRP, e.g., a master ventricle refractory period), and a second ventricular blanking period (e.g., a slave ventricle blanking period). Various events of the master ventricular channel 1530 coincide or occur in coordination with one or more sensed and/or programmed events and/or periods of one or more other channels. Further, some of the events or periods of the master channel 1530 are optional depending, for example, on one or more sensed and/or programmed events.

The exemplary scheme 1500 also includes a slave ventricular channel 1540. The slave ventricular channel 1540 includes an atrial blanking period, a first alert period, a master blanking period, a second alert period, a slave ventricle pace event, a slave ventricle blanking period, and a ventricular refractory period (VRP, e.g., a slave ventricle refractory period). Various events of the slave ventricular channel 1540 coincide or occur in coordination with one or more sensed and/or programmed events and/or periods of one or more other channels. Further, some of the events or periods of the slave channel 1540 are optional, depending, for example, on one or more sensed and/or programmed events.

Two particular cases are shown with respect to the slave channel 1540 that relate to detection or sensing of activity in the slave ventricle prior to delivery of a master ventricle pace event (e.g., Case I) and detection or sensing of activity in the slave ventricle after delivery of a master ventricle pace event (e.g., Case II). In Case I, the slave ventricle activity occurs in an alert period that lies somewhere between the atrial pace event (or detection/sensing of an intrinsic atrial event) and the scheduled delivery time of a master ventricle pace event. In response to Case I, an exemplary method, device and/or system may deliver a master ventricle pace and/or inhibit any scheduled slave ventricle pace. In delivering a pace to a master ventricle, the exemplary scheme 1500 may act via sensing or detecting to ensure that the pace avoids any vulnerable period (e.g., T wave, etc.). An alternative choice is also to inhibit master channel. In Case II, the slave ventricle activity occurs in an alert period that lies somewhere between the master ventricle pace event and a scheduled slave ventricle pace event, for example, the alert period may be coextensive with a VV delay. In response to Case II, an exemplary method, device and/or system may inhibit the scheduled slave ventricle pace event.

The exemplary slave channel 1540 also shows a master ventricle to slave ventricle conduction period (e.g., as determined by PIVCD-RL, PIVCD-LR, etc.). In this example, the ventricular refractory period extends to times greater than the master ventricle to slave ventricle conduction period as measured from delivery of a master pace event. The refractory period may be represented by the following equation (Eqn. 13):

$$VRP_{slave\ Ventricle} > \text{PIVCD-RL or PIVCD-LR} - VV \quad (13)$$

In Eqn. 13, the $VRP_{slave\ Ventricle}$ follows the scheduled slave ventricle pace event.

Various schemes that include one or more features of the exemplary scheme 1500 may help to avoid issues relating to double counting, which may trigger tachycardia therapy. For example, in some implantable devices, a pacing stimulus delivered to one ventricle may be sensed in the other ventricle and be classified as a fast ventricular rhythm (i.e., double counting). In the exemplary scheme 1500, a pacing stimulus generally occurs in the other ventricle before the paced stimulus can be conducted to that ventricle. In other words, the desired VV delay is less than any inherent inter-ventricular conduction and thus, the probability of sensing ventricular paced beats in the alert interval is quite small. In addition, if an auto capture algorithm is used to detect capture of a paced stimulus; then, double counting may be avoided based on such detection.

Figure 16:
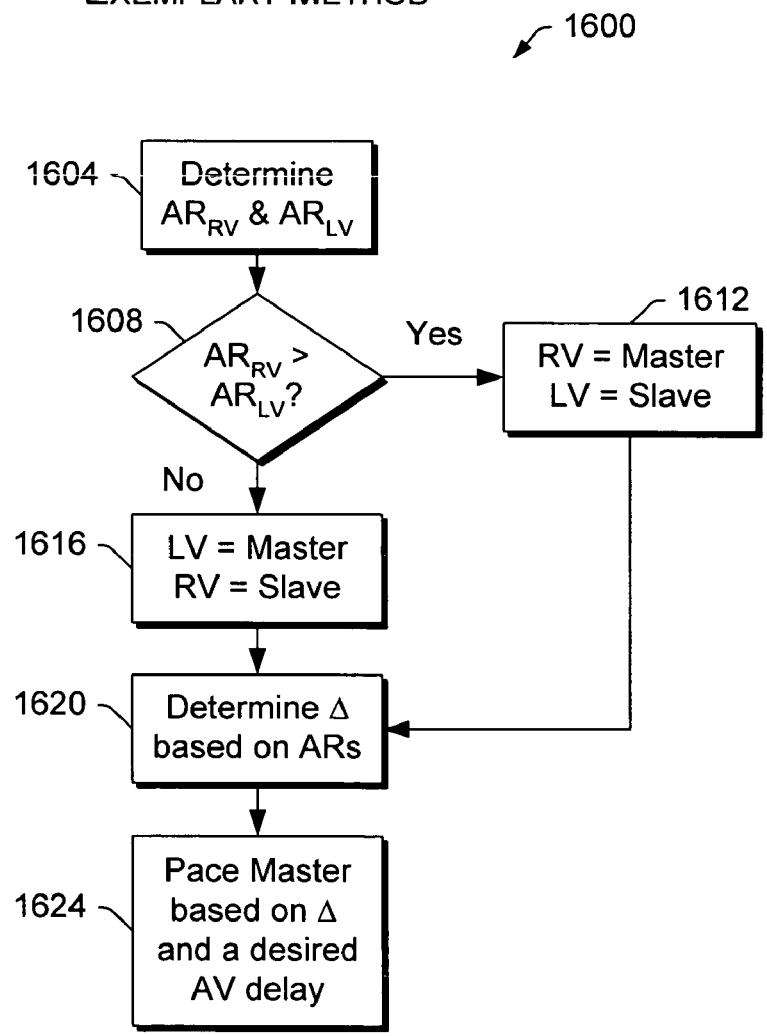
FIG. 16 is a block diagram of an exemplary method for ventricular pacing based on an $AR_{RV}$ time and an $AR_{LV}$ time without an optional correction term.

FIG. 16 shows a block diagram of an exemplary method 1600 for ventricular pacing. In a determination block 1604, an implantable device determines an $AR_{RV}$ time and an $AR_{LV}$ time or equivalent times wherein one or both rely on detection of an intrinsic atrial event. A decision block 1608 follows wherein a decision is made as to whether $AR_{RV}$ is greater than $AR_{LV}$. If $AR_{RV}$ exceeds $AR_{LV}$, then in a set block 1612, the right ventricle is set to the master and the left ventricle is set to the slave. If $AR_{LV}$ exceeds $AR_{RV}$, then in a set block 1616, the left ventricle is set to the master and the right ventricle is set to the slave. Both set blocks 1612, 1616 continue in a determination block 1620 which determines a $\Delta$ value based on the $AR_{RV}$ and $AR_{LV}$ times. A pace master block 1624 follows wherein the master ventricle is paced based on the $\Delta$ and a desired AV delay. The desired AV delay may be determined, for example, based on an echocardiogram or other study. The AV delay is optionally determined by an implantable device based on sensed information.

Thus, as described with respect to FIG. 16, such an exemplary method includes determining an atrial to ventricular activation time for a right ventricle; determining an atrial to ventricular activation time for a left ventricle; and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle wherein pacing of the prior activated ventricle occurs based at least in part on a difference between the time for the right ventricle and the time for the left ventricle and a desired atrio-ventricular delay. In some instances, an inter-ventricular delay may be used instead of, or in addition, to one or more atrial to ventricular activation times.

Figure 17:
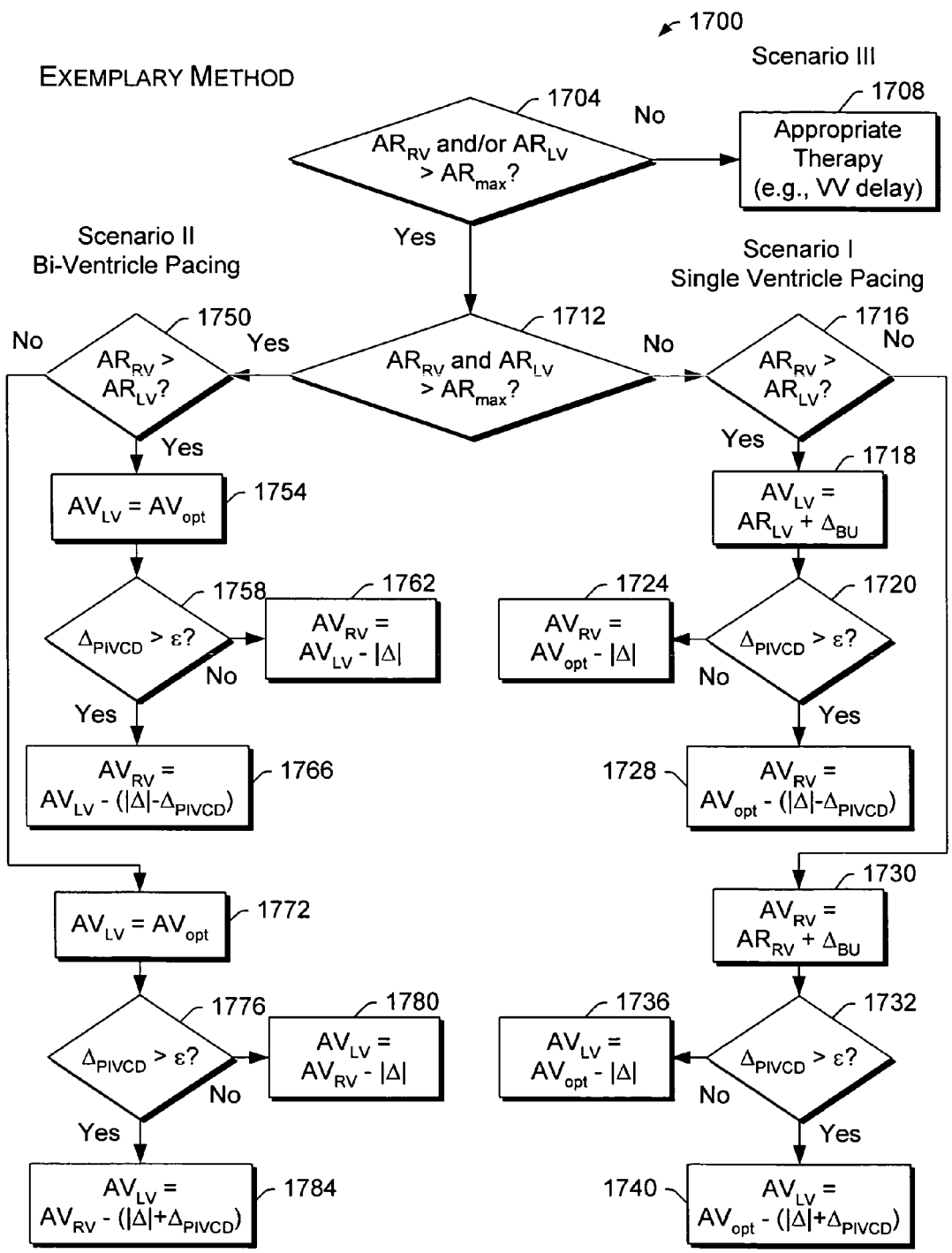
FIG. 17 is a block diagram of an exemplary method for ventricular pacing.

FIG. 17 shows a block diagram of an exemplary method 1700. While the method 1700 pertains to atrial pacing, such a method may omit atrial pacing (e.g., rely on an intrinsic atrial activity, etc.) and/or include atrial pacing and intrinsic atrial activity, etc. (e.g., PR, AR, AV, and/or PV). The exemplary method 1700 includes Scenarios I, II and III as presented above. For example, in a decision block 1704 a decision is made as to whether $AR_{RV}$ and/or $AR_{LV}$ have exceeded a predetermined $AR_{max}$ value. If neither value exceeds $AR_{max}$, then Scenario III follows in no ventricular pacing or other appropriate therapy block 1708. Other appropriate therapy optionally includes therapy that achieves a desirable VV delay. If however one or both values exceed $AR_{max}$, then the method 1700 continues in another decision block 1712. The decision block 1712 decides whether $AR_{RV}$ and $AR_{LV}$ have exceeded $AR_{max}$. If both values do not exceed $AR_{max}$, then single ventricular pacing occurs, for example, Scenario I. If both values exceed $AR_{max}$, then bi-ventricular pacing occurs, for example, Scenario II.

Scenario I commences with a decision block 1716 that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing, the method 1700 continues in a back-up pacing block 1718 where $AV_{LV}$ is set to $AR_{LV}$ plus some back-up time (e.g., $\Delta_{BU}$). The block 1718, while optional, acts to ensure that pacing will occur in the left ventricle if no activity occurs within some given interval. The method 1700 then continues in a decision block 1720 where, if appropriate, a decision is made as to whether $\Delta_{PIVCD}$ exceeds some value $\epsilon$. If the decision block 1720 decides that $\Delta_{PIVCD}$ is small, then in a set block 1724, the method 1700 sets the $AV_{RV}$ delay to $AV_{optimal}-|\Delta|$. Otherwise, the method 1700 uses $\Delta_{PIVCD}$ as a correction factor in a set block 1728, which sets $AV_{RV}$ delay to $AV_{optimal}-(|\Delta|-\Delta_{PIVCD})$.

For left ventricular pacing, the method 1700 continues in a back-up pacing block 1730 where $AV_{LV}$ is set to $AR_{LV}$ plus some back-up time (e.g., $\Delta_{BU}$). The block 1730, while optional, acts to ensure that pacing will occur in the left ventricle if no activity occurs within some given interval. The method 1700 then continues in a decision block 1732 where, if appropriate, a decision is made as to whether $\Delta_{PIVCD}$ exceeds some value $\epsilon$. If the decision block 1732 decides that $\Delta_{PIVCD}$ is small, then in a set block 1736, the method 1700 sets the $AV_{LV}$ delay to $AV_{optimal}-|\Delta|$. Otherwise, the method 1700 uses $\Delta_{PIVCD}$ as a correction factor in a set block 1740, which sets $AV_{LV}$ delay to $AV_{optimal}-(|\Delta|+\Delta_{PIVCD})$.

If the decision block 1712 decides that bi-ventricular pacing is appropriate, for example, Scenario II, then the method 1700 continues in a decision block 1750, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 1700 continues in a set block 1754 which sets $AV_{LV}$ to $AV_{optimal}$. A decision block 1758 follows where, if appropriate, a decision is made as to whether $\Delta_{PIVCD}$ exceeds some value $\epsilon$. If the decision block 1758 decides that $\Delta_{PIVCD}$ is small, then in a set block 1762, the method 1700 sets the $AV_{RV}$ delay to $AV_{LV}-|\Delta|$. Otherwise, the method 1700 uses $\Delta_{PIVCD}$ as a correction factor in a set block 1766, which sets $AV_{RV}$ delay to $AV_{LV}-(|\Delta|-\Delta_{PIVCD})$.

For left ventricular master pacing, the method 1700 continues in a set block 1772 which sets $AV_{RV}$ to $AV_{optimal}$. A decision block 1776 follows where, if appropriate, a decision is made as to whether $\Delta_{PIVCD}$ exceeds some value $\epsilon$. If the decision block 1776 decides that $\Delta_{PIVCD}$ is small, then in a set block 1780, the method 1700 sets the $AV_{LV}$ delay to $AV_{RV}-|\Delta|$. Otherwise, the method 1700 uses $\Delta_{PIVCD}$ as a correction factor in a set block 1784, which sets $AV_{LV}$ delay to $AV_{RV}-(|\Delta|+\Delta_{PIVCD})$.

If a parameter such as the aforementioned a parameter is available, then such a parameter is optionally used to further adjust and/or set one or more delays, as appropriate (see, e.g., Eqns. 10 and 11).

Figure 18:
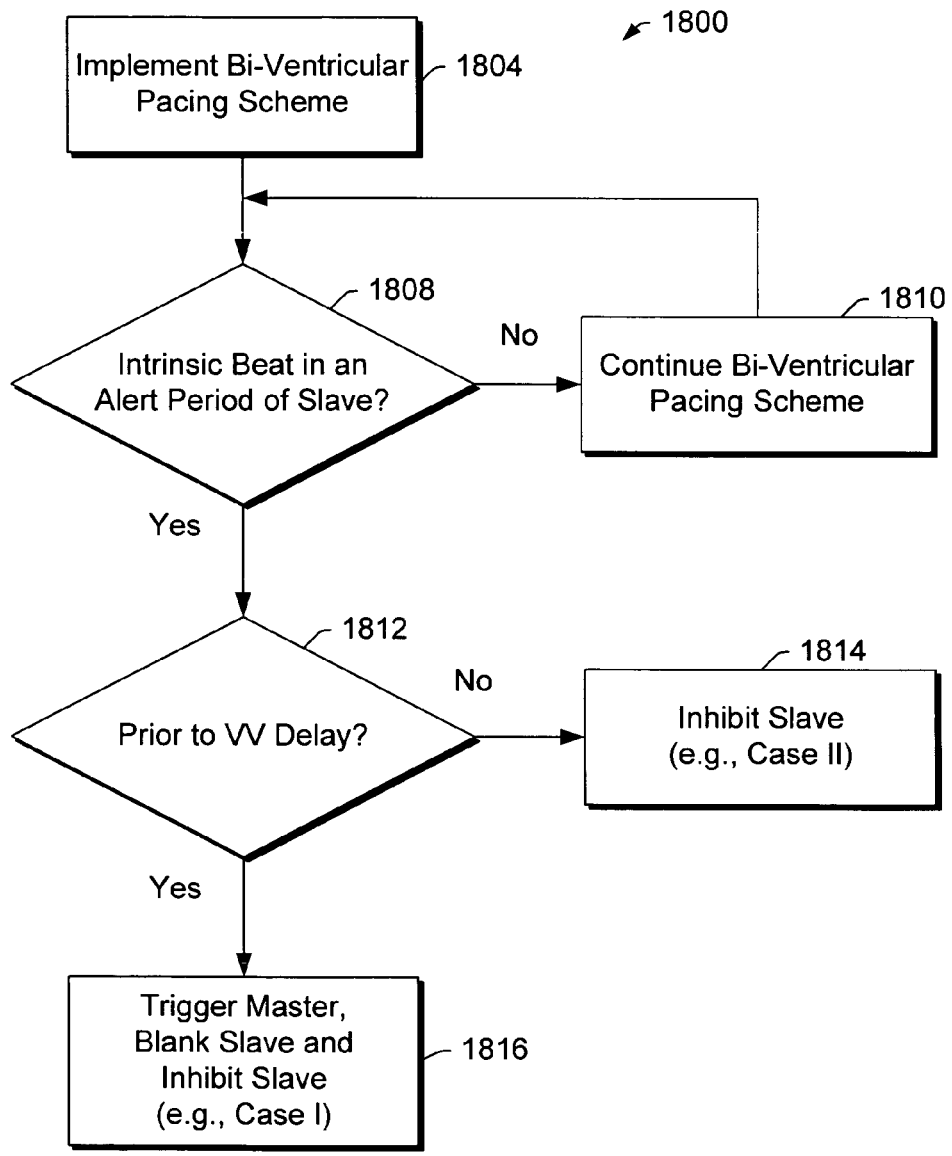
FIG. 18 is a block diagram of an exemplary method corresponding to the scheme of FIG. 15 for immediate delivery of a master stimulation and/or inhibition of a slave stimulation based on the presence and timing of intrinsic beats.

FIG. 18 shows a block diagram of an exemplary method 1800 that optionally relates to the exemplary scheme 1500 of FIG. 15. In an implementation block 1804, a bi-ventricular pacing scheme is implemented. A decision block 1808 follows wherein a decision is made as to whether an intrinsic event has occurred in an alert period of a ventricular channel (e.g., a slave channel). If the decision block 1808 decides that no activity or event has occurred in an alert period, then the method 1800 proceeds to a continuation block 1810 where the bi-ventricular pacing scheme continues where, as appropriate, the method 1800 flows back to the decision block (e.g., after certain programmed events, etc.). However, if the decision block 1808 decides that an intrinsic event occurred in an alert period, then another decision block 1812 follows. The decision block 1812 decides if the activity or event occurred prior to a VV delay period (e.g., a $\Delta_{programmed}$). If the decision block 1812 decides that the occurrence was not prior to a VV delay period then the method 1800 continues in an inhibition block 1814 that inhibits delivery of a pace event to a ventricle (e.g., to a slave ventricle, see Case II of FIG. 15). However, if the decision block 1812 decides that the occurrence was prior to a VV delay period then the method 1800 continues in a trigger, blank and inhibition block 1816. The trigger, blank and inhibition block 1816 acts to trigger delivery of a pace to a ventricle (e.g., a master ventricle), to initiate one or more blanking periods (e.g., atrial and/or ventricular), and to inhibit delivery of a pace to another ventricle (e.g., a slave ventricle).

Of course, an alert period for a master ventricular channel may exist wherein an intrinsic event in the master ventricle causes inhibition of a scheduled pace event in the master ventricle and causes an update in the timing of a scheduled slave pace event. For example, if an intrinsic event is sensed or detected in the master ventricle, then the VV delay may commence in response thereto. Such an exemplary method would act to preserve the VV delay (e.g., $\Delta_{programmed}$) to ensure appropriate timing of contractions in left and right ventricles.

Various exemplary methods, devices and/or systems include setting an interchamber delay between a master chamber and a slave chamber. For example, an interventricular delay may determine timing of ventricular events while an interatrial delay may determine timing of atrial events. Accordingly, an exemplary method includes setting an interchamber delay between a master chamber and a slave chamber, sensing for cardiac activity, if the sensing senses intrinsic activity in the slave chamber, determining whether the intrinsic activity occurred during the interchamber delay, and if the intrinsic activity occurred before the interchamber delay, immediately delivering stimulation to the master chamber.

With respect to the ventricles, an exemplary method includes setting an interventricular (VV) delay between a master ventricle and a slave ventricle (e.g., setting $\Delta_{programmed}$) and sensing for ventricular activity. If activity is sensed in the slave ventricle prior to the VV delay period and hence prior to delivery of a pace to the master ventricle, then immediately delivering stimulation to the master ventricle and inhibiting delivery of stimulation to the slave ventricle. If activity is sensed in the slave ventricle after delivery of stimulation to the master ventricle and prior to expiration of the VV delay, then the exemplary method may inhibit delivery of stimulation to the slave ventricle. Such a method optionally includes adjusting the ventricular refractory period in the slave ventricle channel to be greater than the appropriate PIVCD minus VV. PIVCD could be either PIVCD-LR or PIVCD-RL or average of the two.

An exemplary implantable device includes a power supply, a processor, a lead including one or more electrodes capable of being positioned proximate to a master ventricle, a lead including one or more electrodes capable of being positioned proximate to a slave ventricle, and control logic, executable through use of the processor, to set an interventricular delay between the master ventricle and the slave ventricle and to call for immediate delivery of stimulation to the master ventricle using the lead proximate to the master ventricle upon detection of intrinsic activity in the slave ventricle prior to the interventricular delay (e.g., prior to delivery of stimulation to the master ventricle). Such control logic optionally inhibits delivery of stimulation to the slave ventricle.

Various exemplary methods, devices and/or systems may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation (Eqn. 14) may be used in such a situation:

$$AV_{LV}=AR_{RV}-|\Delta| \text{ or } PV_{LV}=PR_{RV}-|\Delta| \tag{14}$$

With respect to backup pulses, a backup pulse (e.g., for purposes of safety, etc.) may be set according to the following equation (Eqn. 15):

$$AV_{RV}=AR_{RV}+|\gamma| \text{ or } PV_{RV}=PR_{RV}+|\gamma| \tag{15}$$

Of course, administration of a backup pulse may occur upon one or more conditions, for example, failure to detect activity in the particular ventricle within a given period of time. In Eqn. 15, the parameter $\gamma$ is a short time delay, for example, of approximately 5 ms to approximately 10 ms.

According to Eqn. 14, there may not be an a priori need for a particular $AV_{optimal}$ or $PV_{optimal}$. Instead, a need may exist for one or more limits to determine if a sensed AR or PR may be considered normal or acceptable. Further, in such exemplary methods, devices and/or systems, an alert period may be implemented wherein sensing or detection of an intrinsic event in a channel associated with the scheduled pace event causes inhibition of the pace event. For example, if an alert period exist prior to the scheduled pace event and intrinsic activity is detected then inhibition of the pace event may occur, which may act to conserve energy of an implanted device. However, if the alert period expires without sensing or detecting intrinsic activity, the back up pacing pulse in the right ventricle is delivered at $AV_{RV}$ and $AV_{LV}$ will be kept scheduled.

In many instances, heart condition will affect $AR_{RV}$ and $AR_{LV}$, and PIVCD, which, in turn, may affect an existing optimal VV delay setting. Various exemplary methods, devices and/or systems include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, PIVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional. Further, use of internal measurement or sensing equipment for sensing pressure or other indicators of hemodynamic performance is optional. Again, adjustment and learning may rely on IEGM information and/or cardiac other rhythm information.

An exemplary method relies on an atrial to right ventricular conduction time, an atrial to left ventricular conduction time and a $\alpha$ parameter, for example, as described above, to determine an optimal AV delay and/or VV delay. Another exemplary method relies on an atrial to right ventricular conduction time, an atrial to left ventricular conduction time and a limit that may be used to decide whether one or more of the conduction times are acceptable. In these examples, an interventricular conduction time may be used in lieu of an atrial to ventricular conduction time, for example, where ventricular activity originates with a common atrial event.

According to various exemplary methods, devices and/or systems, information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices and/or systems include determining an optimal interventricular delay (e.g., $\Delta_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device and/or system includes use of internal sensors to measure and/or update such an optimal delay and/or to determine values for one or more parameters related to an optimal delay. For example, a blood pressure sensor (e.g., aortic arch, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

CONCLUSION

Although exemplary methods, devices and/or systems have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices and/or systems.

What is claimed is:

1. A method comprising:
   detecting intrinsic ventricular activity of a right ventricle;
   detecting intrinsic ventricular activity of a left ventricle;
   computing a time difference between the intrinsic ventricular activity of the right ventricle and the intrinsic ventricular activity of the left ventricle;
   delivering a pacing pulse to one of the right and left ventricles and measuring corresponding intrinsic activity of the other of the right and left ventricles, and computing a second time difference between the pacing pulse and the corresponding intrinsic activity;
   determining a pacing interval for a v-v delay based at least in part on the time difference between the ventricular activity of the right ventricle and the ventricular activity of the left ventricle, wherein the pacing interval for the v-v delay is set as a function of the time difference between the ventricular activity of the right ventricle and the ventricular activity of the left ventricle and as a function of the second time difference between the pacing pulse and the corresponding intrinsic activity; and
   delivering one or more pacing pulses to at least one of the right and left ventricles based on the pacing interval.

2. The method of claim 1 wherein:
   detecting ventricular activity in a right ventricle comprises detecting electrical activity.

3. The method of claim 1 and further comprising:
   determining a pacing sequence that paces the right ventricle first if the time for the right ventricle exceeds the time for the left ventricle or that paces the left ventricle first if the time for the left ventricle exceeds the time for the right ventricle.

4. The method of claim 3, wherein the determining a pacing sequence relies at least in part on a predetermined atrio-ventricular delay.

5. The method of claim 1, wherein computing a time difference comprises determining an absolute value of the difference between the ventricular activity time for the right ventricle and the ventricular activity time for the left ventricle.

6. The method of claim 3, wherein determining the pacing sequence comprises pacing the latter activated ventricle to achieve a predetermined atrio-ventricular delay.

7. The method of claim 1, wherein detecting ventricular activity for the right and left ventricles comprises using a single sense amplifier.

8. An implantable device comprising:
   means for detecting intrinsic ventricular activity of a right ventricle;
   means for detecting intrinsic ventricular activity of a left ventricle;
   means for computing a time difference between the intrinsic ventricular activity of the right ventricle and the intrinsic ventricular activity of the left ventricle;
   means for delivering a pacing pulse to one of the right and left ventricles and means for measuring corresponding intrinsic activity of the other of the right and left ventricles, and means for computing a second time difference between the pacing pulse and the pulse and the corresponding intrinsic activity; and
   means for determining a pacing interval for a v-v delay based at least in part on the time difference between the ventricular activity of the right ventricle and the ventricular activity of the left ventricle comprising means for setting the pacing interval for the v-v delay as a function of the time difference between the ventricular activity of the right ventricle and the ventricular activity of the left ventricle and as a function of the second time difference between the pacing pulse and the corresponding intrinsic activity.

9. The implantable device of claim 8 and further comprising:
   means for determining a pacing sequence that paces the right ventricle first if the time for the right ventricle exceeds the time for the left ventricle or that paces the left ventricle first if the time for the left ventricle exceeds the time for the right ventricle.

10. The implantable device of claim 9, wherein the means for determining a pacing sequence comprises means for relying on a predetermined atrio-ventricular delay.

11. The implantable device of claim 9, wherein the means for determining the pacing sequence comprises means for pacing the latter activated ventricle to achieve a predetermined atrio-ventricular delay.

12. The implantable device of claim 8, wherein the means for computing a time difference comprises means for determining an absolute value of the difference between the ventricular activity for the right ventricle and the ventricular activity for the left ventricle.

13. The implantable device of claim 8, wherein the means for detecting ventricular activity for the right and left ventricles comprises a single sense amplifier.

14. An implantable device comprising:

a power supply;

at least one lead comprising one or more electrodes capable of being positioned within a patient's body to sense activity of a right ventricle and of a left ventricle; and a processor that is operative to receive activity signals from the at least one lead to detect intrinsic ventricular activity of the right ventricle and intrinsic ventricular activity of the left ventricle, to compute a time difference between the ventricular activity of the right and left ventricles, to deliver a pacing pulse to one of the right and left ventricles and measure corresponding intrinsic activity of the other of the right and left ventricles, compute a second time difference between the pacing pulse and the corresponding intrinsic activity, and to determine a pacing interval for a v-v delay based at least in part on the time difference, wherein the pacing interval for the v-v delay is set as a function of the time difference between the ventricular activity of the right ventricle and the ventricular activity of the left ventricle and as a function of the second time difference between the pacing pulse and the corresponding intrinsic activity.

\* \* \* \* \*